United States Patent [19]

Warren et al.

[11] Patent Number: 4,671,959

[45] Date of Patent: Jun. 9, 1987

[54] METHOD OF CAUSING THE REDUCTION OF PHYSIOLOGICAL AND/OR SUBJECTIVE REACTIVITY TO STRESS IN HUMANS BEING SUBJECTED TO STRESS CONDITIONS

[75] Inventors: Craig B. Warren, Rumson, N.J.; Marina A. Munteanu, New York, N.Y.; Gary E. Schwartz, Guilford, Conn.; Carlos Benaim, Hartsdale; Henry G. Walter, Jr., Mill Neck, both of N.Y.; Ronald S. Leight, Aberdeen; Donald A. Withycombe, Lincroft, both of N.J.; Braja D. Mookherjee, Holmdel; Robert W. Trenkle, Bricktown, both of N.J.

[73] Assignees: Yale University, New Haven, Conn.; International Flavors & Fragrances Inc., New York, N.Y.

[21] Appl. No.: 858,728

[22] Filed: May 2, 1986

Related U.S. Application Data

[60] Division of Ser. No. 800.428, Nov. 21, 1985, which is a continuation-in-part of Ser. No. 671,608, Nov. 14, 1984.

[51] Int. Cl.⁴ .................. A61K 35/78; A61K 7/26; A61K 31/335
[52] U.S. Cl. .................. 424/195.1; 252/522 R; 424/49; 424/58; 426/534; 426/536; 514/464; 514/810; 514/812; 514/901; 514/958
[58] Field of Search ............... 424/195.1; 514/464

[56] References Cited

U.S. PATENT DOCUMENTS

| 64,421 | 5/1867 | Holtzermann | 424/195.1 |
|---|---|---|---|
| 90,308 | 5/1869 | Robinson | 424/195.1 |
| 101,042 | 3/1870 | Rinkle | 424/195.1 |
| 111,821 | 2/1871 | Danforth | 424/58 |
| 115,547 | 5/1871 | Walton | 424/195.1 |
| 380,700 | 4/1888 | Schwartz | 424/58 |
| 1,943,467 | 2/1932 | Bley | 424/50 |
| 4,198,393 | 4/1980 | Yoshida et al. | 424/49 |
| 4,404,184 | 9/1983 | Pittet et al. | 424/49 |
| 4,420,472 | 12/1983 | Boden et al. | 424/58 |
| 4,430,323 | 2/1984 | Silver | 424/52 |
| 4,454,111 | 6/1984 | Boden et al. | 424/58 |

FOREIGN PATENT DOCUMENTS

| 1098166 | 1/1961 | Fed. Rep. of Germany | 424/58 |
|---|---|---|---|
| 5738708 | 3/1982 | Japan | 424/58 |

OTHER PUBLICATIONS

Pereira (1854) Elements of Materia Medica, pp. 411–416 (esp. 415) "Nutmegs".
Cotton (1963) Old Mr. Boston De Luxe Official Bartenders Guide "Eggnog" pp. 114-115e.
Jacobs (1953) Am.Perf.Essential Oil Review 61:469-47-1-389-391-393 Flavoring Mouthwashes and Flavoring Toothpaste.
Arctander (1960) Perfume & Flavor Materials of Natural Orig. pp. 441–445 Nutmeg 391-392 Mace.
Arctander (1969) Perfume & Flavor Chemicals II:2291 Myristicin.

(List continued on next page.)

*Primary Examiner*—Shep K. Rose
*Attorney, Agent, or Firm*—Arthur L. Liberman

[57] ABSTRACT

Described is a method for reducing physiological and/or subjective reactivity to stress in humans being subjected to stress conditions. The method consists of administering to such humans an effective amount of a physiological and/or subjective stress reactivity-reducing substance selected from the group consisting of:

(i) Nutmeg Oil;
(ii) Mace Extract;
(iii) Neroli Oil;
(iv) Valerian Oil;
(v) Myristicin;
(vi) Isoelemicin; and
(vii) Elemicin.

Administration is through inhalation or transdermally using one or more of the above ingredients alone or in a suitable composition such as ethanol and/or a perfume composition, cologne or perfumed article (e.g., air freshener or deodorant stick). Also described is a method for detecting the reduction of physiological and/or subjective reactivity to stress in a human.

1 Claim, 6 Drawing Figures

OTHER PUBLICATIONS

Farnsworth Science 152:1086–1092, Dec. 6, 1968, Hallucinogenic Plants, esp. p. 1088 Nutmeg, Myristicin.

Fras, New York State Journal of Medicine 69(3):463–465 (1969) Hallucinogenic Effects of Nutmeg in Adolescent.

Weil, Journal of Psychedelic Drugs 3 (2):72–80, Spring 1971 Nutmeg As a Psychoactive Drug.

de Mello, Psychopharmacologia 31:349–363 (1973) Behavioral Observations on Compounds Found in Nutmeg.

Sherry, et al, Experimental 34(4):492–393 (1978) Enhancement of Ethanol–Induced Sleep By Whole Oil of Nutmeg.

Faguet, AM.J. Psychiatry 135(7):860–861, Jul. 1975 "Spice Cabinet" Intoxication.

Nitto Electric Industries, Co. (Sasali, et al), Japan Kokai Tokkyo Koho 59/55821 (copy of translation and actual Japanese Patent).

Nitto Electric Industries, Co. (Sawaguchi, et al), Japan Kokai Tokkyo Koho 59/55827 (copy of translation and actual copy of Japanese Patent).

GLC PROFILE FOR EXAMPLE I.

GLC PROFILE FOR BULKED FRACTIONS 7-12 OF EXAMPLE I.

EXAMPLE III
EFFECT ON BLOOD PRESSURE

METHOD OF CAUSING THE REDUCTION OF PHYSIOLOGICAL AND/OR SUBJECTIVE REACTIVITY TO STRESS IN HUMANS BEING SUBJECTED TO STRESS CONDITIONS

This is a divisional of application Ser. No. 800,428, filed 11/21/85, which, in turn, is a continuation-in-part application of U.S. Ser. No. 671,608 filed on Nov. 14, 1984.

INTRODUCTION

This invention relates to a process for reducing physiological and/or subjective reactivity to stress in humans subjected to stress conditions. The process involves administering to said humans an effective amount of a stress reactivity-reducing substance hereinafter described.

The term "stress" hereinafter refers to an event or experience in the life of an individual that has specific physiologic and/or subjective consequences that disturb the equilibrium of the individual (Glock, C. Y. & Leonard, H. L., Journal of Chronic Diseases, 1956, 5, 179). Sources of stress may be an individual's occupation, for example, controlling air traffic at a busy airport, or it may be a life event change such as a change of job, a death in the family or a divorce, or it may be the small irritations and strains of everyday life—the daily hassles.

The term "reactivity" hereinafter refers to the change generated by stress in the individual's physiologic and/or subjective condition. Within the context of this invention, "reactivity" may be ascertained objectively by measuring change in systolic blood pressure relative to equilibrium blood pressure resulting from the application of stress. The term "physiologic change" has been employed herein to identify this form of reactivity.

Unlike a drug that is ingested orally or injected subcutaneously, the substances used for the practice of our invention are inhaled and/or absorbed by means of transdermal penetration. Hence, for the purpose of practicing our invention, the term "amount administered" hereinafter is intended to mean "amount of stress reactivity-reducing composition calculated to have been breathed in, retained and absorbed into the bloodstream or transdermally absorbed into the bloodstream".

For the purposes of this invention, a statistically significant increase in systolic blood pressure ($p < 0.1$), is generally 3 mm/Hg or more due to the stress.

Hereinafter, the subjective reactivity to stress is a statistically significant change ($p < 0.05$) in the individual's self-report of one or more of the following emotions:
Decrease in degree of relaxation;
Decrease in happiness;
Decrease in calmness;
Increase in fear;
Increase in tenseness;
Increase in embarrassment;
Increase in anger; and/or
Increase in anxiety.

Reactivity to stress varies with the individual. Some individuals thrive on stress whereas in other individuals, the same stress drives them towards sickness (Executive Fitness Newsletter, Rodale Press Inc., Vol. 15, No. 17 [1984]). "Reactivity" hereinafter refers to a negative reaction to stress.

"Reactivity" to stress should not be confused with the abnormally high base-line blood pressure or anxiety levels which may require drug treatment. For example, it should not be confused with hypertension which is defined as blood pressure that remains consistently above 140 mm/Hg systolic and 90 mm diastolic pressure with repeated blood pressure determinations over the course of several weeks (Report of the Joint National Committee on Detection, Evaluation and Treatment of High Blood Pressure; Journal of the American Medical Association, 1977, 277, 255–261).

It is appreciated that reactivity and hypertension or state of anxiety may be related. Abnormal anxiety or depression has as its major primary causative components the fundamental conditions of helplessness, uncertainty, anticipation, undirected arousal and the like (Zucker, M. & Spielberger, C. D., "Emotions and Anxiety", Lawrence Erlbaum Associates, Publishers; Hillsdale, New Jersey [1976]). See, also, The Diagnostic and Statistical Manual of the American Psychiatric Association, DSM3, 1980.

BACKGROUND OF THE INVENTION

Reactivity to stress is insidious because it does not directly incapacitate a human. Researchers are discovering that stress decreases productivity, and eventually may lead to illness. As mentioned above, this reactivity to stress can be brought about by the daily hassles—the repeated or chronic strains of everyday life. Research in this area has shown that the daily hassle, as measured by self-report, is more strongly associated with somatic health than are life event scores. That is, the frequency and intensity of hassles are significantly related to somatic illness (A. Delongis, et al, Health Psychology, 1981, 1 (2), 119–136).

Chronic reactivity, as measured by elevated blood pressure, particularly systolic blood pressure, is correlated with disease. By use of a portable blood pressure-measuring device, it has been shown that regularly recurring stress (specifically that occurring in the work place) correlates with the occurrence of left ventricular hypertrophy. In particular, it was shown that the correlation exists in patients showing elevated systolic blood pressures while actually engaged in their workday tasks (R. B. Devereux, et al, Circulation 68, No. 3, 470–476, 1983). In another study, blood pressures measured every 15 minutes for 24 hours in 25 normal subjects, 25 borderline subjects and 25 established hypertensive subjects showed significantly higher blood pressures at work than at home, at the physician's office or while sleeping. (T. G. Pickering, et al, Clinical and Experimental Hypertension, A4(4& 5), 675–693 [1982]).

The classical techniques used for controlling reactivity to stress include biofeedback, meditation and drugs.

With respect to biofeedback, Benson, et al, cited infra, used the constant-cuff technique and gave feedback and reinforcement for the lowering of systolic blood pressure in seven patients, five of whom had been diagnosed as having essential hypertension. The five patients with hypertension responded positively, all showing significant decreases in their systolic blood pressures after 30 sessions of training (Benson, H., Shapiro, D., Tursky, B., and Schwartz, G. E., Science, 1971, 173, 740–742).

Other physiological parameters used for biofeedback training include pulse transit time, electromyogram activity and skin resistance biofeedback.

The type of relaxation training techniques used for the treatment of hypertension are variations of either certain Eastern meditative disciplines, progressive relaxation techniques or autogenic training. These techniques are intended to lower blood pressure by promoting physical and mental relaxation. For example, the Benson relaxation response technique (Benson, H., et al, Psychiatry, 1974, 37, 37–46) was used to lower the blood pressures of 22 untreated borderline hyptertensive patients and 14 pharmacologically-treated hypertensives. Mean blood pressure during a 6-week baseline was 147/95 mm/Hg for the untreated patients and 146/92 for the treated patients. After 25 weeks of meditation-relaxation, blood pressure reductions of 8/4 mm/Hg and 11/5 mm/Hg were reported for the untreated and treated patients, respectively. A review of the use of biofeedback and relaxation techniques for the treatment of hypertension can be found in: Surwit, et al, "Behavioral Approaches to Cardiovascular Disease", Behavorial Medicine Series, Academic Press, 1982, 139–156.

Man has also sought chemical agents to modify the effects of stress, tension, anxiety and dysphoria throughout recorded history. Probably, the oldest drug for this use is ethanol. In the last century, bromide salts and the barbiturates were introduced. Barbiturates continued to be the dominant anti-anxiety agents until the 1950's when propandiol carbamates (MEPROBAMATE®), and congeners were introduced. The side effects of the barbiurates and the propandiol carbamates, in particular, the physical dependence caused by thse drugs and the severe accute intoxication on overdosage, encouraged the search for more specific anti-anxiety drugs. Chlordiazepoxide (LIBRITABS®) was discovered in the late 1950's followed by chlordiazepoxide hydrochloride (LIBRIUM®), diazepam (VALIUM®), Lorazepam (ATRIVAN®) and some dozen other benzodiazepine congeners. Today the bezodiazepines series of drugs, chlordiazepoxide and diazepam in particular, are the major drugs used for treatment of anxiety and stress. A review of the drug treatment of stress and anxiety can be found in: Goodman and Gilman," Pharmacological Basis of Therapeutics", 6th ed., MacMillan Publishing Co., New York, N.Y., (1980), pages 436–446.

The current pharmacologic treatment of hypertension is based on the "stepped-care" approach. When blood pressure remains above 140/90 mm/Hg., the first step is to place the patient on a thiazide diuretic. If the diuretic does not achieve reduction of blood pressure, the next step is to add a centrally-acting sympatholytic agent (e.g., Methyldopa) or a $\beta$-andrenergic blocking agent (e.g., propranolol). If the second step does not result in normalization of blood pressure, the third step is to add a directaction vasodilator (e.g., hydralazine). If the third step does not work, a variety of other agents must be devised on a individualized basis for each patient (Surwit, R. S., et al, "Behavioral Approaches to Cardiovascular Disease", Academic Press, New York, page 138 [1982]).

Our invention for the reduction of physiological and/or subjective reactivity to stress differs from the drug approach both in dose level and concept. The dose levels (presented hereinafter) are much lower than those used for the drug therapies presented above (microgram levels vs. milligram levels). The concepts differ in that our invention is for the prevention of surges in systolic blood pressure rather than a cure for a sickness. Unlike biofeedback or meditation, our invention does not require training sessions. However, meditation, like our invention, can be used to control physiological and/or subjective reactivity to stress.

Our invention for stress reactivity reduction utilizes plantderived substances common to the fields of perfumery and aromatherapy. The dose levels, however, differ from those normally employed in either perfumery or aromatherapy and the mode of application differs from those normally employed for aromatherapy and are significantly less. In addition, concern over (minor) blood pressure surges and possibilities for damping such surges appear to be absent in the folk medicine literature.

The term "Aromatherapy" is intended herein to mean the use of plant-derived substances; volatile substances derived from plants for the treatment of health problems. Generally, the volatile fraction—the essential oil fraction—of the plant-derived substance is used. The use of the volatile fractions of plants for treatment of various ailments is reviewed in the following three monographs:

(1) J. Valnet, "The Practice of Aromatherapy", Destiny Books (Division of Inner Traditions International, Ltd.), New York, N.Y., 1982;

(2) R. Tisserand, "The Art of Aromatherapy", Destiny Books (Division of Inner Traditions International, Ltd.), New York, N.Y., 1983; and (3) A. Leung, "Encyclopedia of Common Natural Ingredients", J. Wiley & Sons Publishing Co., New York, N.Y., 1980.

A detailed analysis of the aromatherapy folk medicine literature suggested that a number of essential oils commonly used in perfumery might have a multiplicity of medical effects. Some of these oils are employed in the practice of this invention.

Neroli oil is the essential oil obtained from orange blossoms. Neroli oil has a folk medicine history as being an anti-depressant, aphrodisiac, antiseptic, antispasmodic and of having digestive and sedative activity. The anecdotal literature suggests that neroli oil is an effective sedative and anti-depressant and that it may be used for insomnia, hysteria, states of anxiety and depression (R. Tisserand, "The Art of Aromatherapy", cited, supra). Tisserand further states:

"Neroli is one of the most effective sedative-antidepressant oils: it may be used for insomnia, hysteria, states of anxiety and depression. It calms and slows down the mind. It also has a notable action on the heart, diminishing the amplitude of heart muscle contraction, hence its use in palpitations or other types of cardiac spasm. Derived from this is its use in panicky, hysterial, fearful types of people—those who upset themselves unnecessarily, and become over wrought over nothing. One can also see that neroli is a valuable remedy for shock, or for disorders caused by sudden shock, or fear, causing a strain on the heart. It is valuable in chronic diarrhoea, when this is related to long-standing stress or fear. Its action is slow but sure.

Oil of neroli also has a pronounced action on the skin. Like lavender and geranium it can be used with benefit on any type of skin. It is totally non-irritant and may be used where there is irritation or redness. It is said to be useful for dry skin and broken veins. It is one of the oils which acts on a cellular level stimulating the elimination of old cells and the growth of new ones. Neroli makes a luxurious, relaxing, and deodorant bath oil.

Orange-flower water is soothing, digestive, carminative. It makes a very useful, mild remedy for infants' colic, and its sedative action helps to send them to sleep."

Valerian oil is the essential oil obtained from the root of *Valeriana Officinalis*. The folk medicine literature lists the valerian root (fresh or dried) as being useful as an antispasmodic, carminative, stomachic and sedative. It has been used to treat migraine, insomnia, hysteria, fatigue and stomach cramps that cause vomiting (A. Y. Leung, "Encyclopedia of Common Natural Ingredients", John Wiley & Sons, New York, N.Y., 1980, pages (317-320).

Regarding valerian oil's use in Russia, Hutchens, et al, "Indian Herbalogy of North America", (published by Merco of Windsor, Ontario, Canada), 5th edition, 1974, states:

"Russian Experience: Valeriana is known to Folk Medicine as having a general calming and sedative effect on the central nervous system, to induce sleep and rest, spasms of the stomach, intestines and blood vessels, nervous heart conditions. Further acknowledgement as appetizer, headache relief, hysteria, epilepsy, tape worm, diarrhoea, lose stomach, fever. Externally: Vapour baths given to childern will quieten and encourage restful sleep (Bello-Russ. Academy of Science Minsk, 1965)."

In "Sedative Principles of Valeriana Roots", Hikino, et al, Shoyakugaku Zasshi, 34, (1), 1980, pages 19-24, it is indicated that compounds possessing sedative activity, isolated from valerian roots, have failed to fully account for the sedative activity exhibited by the roots per se. It is further stated therein that, recently, iridoids named valepotriates were isolated as analgesic and sedative principles from Indian valerian roots. In this paper, a correlation between the contents of the valepotriates and the pharmacological activity of various valerian roots was examined. Napalese and Chinese valerian roots containing an appreciable quantity of valepotriates showed no sedative activity, while Japanese valerian root containing less valepotriates inhibited stress-induced ulcer formation and prolonged hexobarbital-induced sleep in mice. An extract of "Hokkai-kisso", i.e., roots of a Japanese valerian, was fractionated and the effect of each of the fractions on the enhancement of hexobarbital anesthesis was tested. Kessyl glycol diacetate, Kessyl glycol 8-acetate and Kessyl glycol 2-acetate were obtained as active principles therefrom. The enhancement of hexobarbital anesthesis by Kessyl glycol diacetate was assumed to be due to its inhibitory effect on the central nervous system. Kessyl glycol diacetate exhibited no inhibitory action on the stress-induced ulcer production.

The chemical constituents, pharmacology and known uses of valerian are reviewed in: "Herbal Remedies Used in Sedative and Antirheumatic Preparations: Part I", Phillipson, et al, The Pharmaceutical Journal, July 21, 1984, pages 80-82.

Another potentially interesting plant substance is nutmeg which was important in medicine as well as in cooking. It was used as a therapeutic by Arab physicians as early as the 7th Century A.D. for treatment for disorders of the digestive system, kidney disease, pain and lymphatic ailments. Nutmeg is a significant item in the Hindu Pharmacopeia wherein it has been prescribed for fever, consumption, asthma and heart disease. Nutmeg is employed by folk practitioners in India as an analgesic and sedative. In large doses (two teaspoons or more of ground nutmeg), nutmeg exhibits mild hallucinogenic activity, the description by Payne (R. B. Payne, New England Journal of Medicine, 269, pages 36-38 [1963]) being illustrative of this activity. Two college students, 19 and 20 years old, each consumed two tablespoons (14 grams of the equivalent of two whole seeds) of powdered nutmeg in milk. About 5 hours later, each had the onset of a leaden feeling in the extremities and a nonchalant detached mental state described as "unreal" or "dreamlike". Rapid heart rates and palpitation were observed and both complained of dry mouth and thirst. See, also, Wiel (A. T. Weil, Ethnopharmacol. Search Psychoact. Drugs [Proc. Symp.], 1967, [Pub. 1979], 188-201).

The fraction of nutmeg responsible for the mild hallucinogenic activity is suggested by the literature to be the aromatic fraction of the oil containing safrole, methyleugenol, eugenol, methylisoeugenol, myristicin, elemicin, isoelemicin and methoxyeugenol as the major components. Of these, myristicin, elemicin and isoelemicin have been reported to be the active molecules (A. T. Shulgin, et al, Ethnopharmacol. Search Psychoact. Drugs [Proc. Symp.], 1967, [Pub. 1979], 202-214). The myristicinelemicin fraction of oil of nutmeg produces many of the activities of crude ground nutmeg but lacks adequate potency to explain the nutmeg intoxication syndrome on a quantitative basis. Nutmeg and synthetically-made myristicin show a mild degree of monoamine oxidase inhibiting activity. The monoamine oxidase activity is found in the volatile component of nutmeg (E. B. Truitt, Jr., Ethnopharmacol. Search Psychoact. Drugs [Proc. Symp.], 1967, [Pub. 1979], 215-222).

Nutmeg oil, known as *myristica fragrans*, or myristicaceae, is the essential oil from the kernel of the fruit of the nutmeg tree. The stone of the fruit is enclosed within a husk which, when dried, is known as mace. "Mace Extract" is an aromatic essence extracted from mace. "Nutmeg Butter" is a fixed oil obtained by hot-pressing the nutmeg kernels, and contains myristine, butyrin, olein, palmitine and stearine. The essence contains 80% pinene and camphene, 8% dipentene, 6% terpenic alcohols, (linalool, borneol, terpineo]and geraniol), 4% myristicin and various substances such as eugenol and safrol. Valnet, "The Practice of Aromatherapy", (supra) states that, for external use:

(a) "nutmeg butter" is used in liniments for the treatment of rheumatic pains and toothaches; and (b) "nutmeg butter" is used in the form of "nerve balm" for treatment of rheumatic pains, the form being a mixture of the essences of rosemary and clove together with nutmeg butter.

A form of nutmeg oil, *Myristica castaneifolia* (Myristacaceae) Fiji is described as possessing biological activity, specifically in the antitumor field, in U.S. Pat. No. 4,352,797 issued on Oct. 5, 1982, the specification for which is incorporated by reference herein. At page 4 of the January/February 1984 (Vol. 6, No. 1) edition of FOCUS (World Wildlife Fund-U.S.), nutmeg is indicated as being an analgesic and a hallucinogen. In the paper "Nutmeg as a Narcotic" by Kalbhen in Angew. Chem. 83, 379 (1971), Kalbhen discloses that the hallucinogenic ingredients of nutmeg include, interalia,:

(i) Myristicin having the structure:

(ii) Elemicin having the structure:

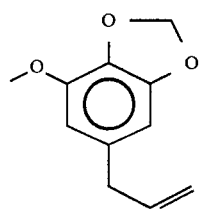

and (iii) Isoelemicin having the structure:

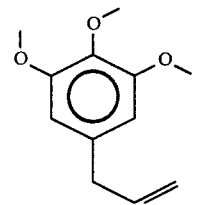

The Kalbhen paper is incorporated herein by reference.

Furthermore, *Myristica fragrans* is disclosed at Chem. Abstracts, Vol. 101, No. 2831 g (abstract of Japan Kokai Tokkyo Koho 59/55,827) as being useful in the field of drug stabilization in conjunction with the utilization of transdermal pharmaceuticals. The said abstract and the said Japanese Kokai Tokkyo Koho are incorporated herein by reference.

Furthermore, isoelemicin having the structure:

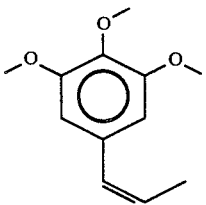

is a known flavor ingredient as set forth in U.S. Pat. No. 3,686,004 issued on Aug. 22, 1972, the specification for which is incorporated by reference herein. By the same token, myristicin having the structure:

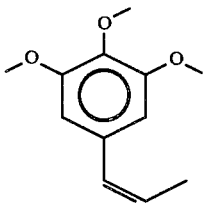

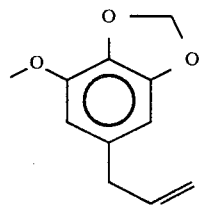

is disclosed as a component of the aroma of blueberries in J. Sci. Food Agric., 1983, 34(9), 992–6 (abstracted at Chem. Abstracts, Vol. 99:174466r). (Hirvi, et al) (Copy of paper incorporated by reference herein)

Furthermore, regarding myristicin, Arctander, "Perfume & Flavor Chemicals (Aroma Chemicals)", published by the author in 1969, states at monograph 2291, that myristicin is:

"Pleasant and warm-balsamic, slightly woody odor of good tenacity. The undiluted material shows some "pepperiness".

This material, although commonly found in natural oils, has found only limited use in perfumery . . . "

The essential oils described above are also common perfumery ingredients as described in Arctander, "Perfume and Flavors Materials of Natural Origin", published by the author in 1960. (Mace extract at columns 391–393; neroli oil at columns 435–437; nutmeg oil at columns 442–445; and valerian oil at columns 637–638).

In summary, the materials employed in the practice of this invention, are known in the art and are known to exhibit physiologic activity. However, insofar as the inventors hereof have been able to ascertain, no suggestion relevant to reducing physiological and/or subjective reactivity to stress is made in the prior art.

OBJECTS OF THE INVENTION

It is an object of our invention to create a method for causing the reduction of physiological and/or subjective reactivity to stress in a human being subjected to stress conditions (such as the daily hassles of the work place).

It is a further object of our invention to develop a method for causing reduction of physiological and/or subjective reactivity to stress in a human being subjected to conditions of stress by administering to such a human an effective amount of an active material in an aesthetically pleasing form.

It is a further object of our invention to cause the reduction of physiological and/or subjective reactivity to stress in a human being subjected to stress conditions by administering transdermally and/or by means of inhalation an effective amount of an active material in an aesthetically pleasing form, such as, for example, a perfumant or an air freshener.

It is a further object of our invention to develop a method for detecting the physiological and/or subjective reactivity to stress in a human.

It is a further object of our invention to develop a method for detecting physiological and/or subjective reactivity to stress in a human using the simultaneous measurement of systolic blood pressure and mood changes resulting from application of stress taken further together with measuring the effect of a postulated stress reactivity-reducing substance.

BRIEF DESCRIPTION OF THE INVENTION

Our invention is concerned with a method for causing the reduction of physiological and/or subjective reactivity to stress in a human subject to stress conditions which comprises the step of administering transdermally or through inhalation to said human an effective physiological and/or subjective stress reactivity-reducing substance which may be one or a combination of any one of the following materials (sometimes referred to herein as "active(s)"):

(i) Nutmeg oil;
(ii) Mace extract;
(iii) Neroli oil;
(iv) Valerian oil;
(v) Myristicin;
(vi) Elemicin; and
(vii) Isoelemicin.

The active(s) can be administered alone or as part of a composition which may include ethyl alcohol and/or perfumes. Perfumed articles may be employed to apply the actives. Examples of such perfumed articles are solid or liquid anionic, cationic, nonionic or zwitterionic detergents, fabric softener compositions, fabric softener articles, cosmetic powders, hair preparations, deodorant sticks, air fresheners and perfumed polymers.

Specifically, with regard to dose levels, the "actives" are to be divided into two groups:

Group "ALEPH"

Nutmeg oil;
Mace Extract;
Neroli oil; and
Valerian oil
   (taken alone or in combination).

Group "BETH"

Myristicin;
Elemicin; and
Isoelemicin
   (taken alone or in combination).

The Group "ALEPH" dose or amount administered, for the purpose of our invention, is from about 13 micrograms up to about 1000 micrograms. The Group "BETH" dose or amount administered, for the purpose of our invention, is from about 0.013 micrograms up to about 50 micrograms. When Groups "ALEPH" and "BETH" are used in combination, the dosage or amount administered is from about 0.013 micrograms up to about 1000 micrograms with an upper limit of the Group "BETH" "actives" within said combination being at about 50 micrograms.

The term "amount administered" is intended herein to mean "amount calculated to have been breathed in, retained and absorbed into the bloodstream or transdermally absorbed into the bloodstream". The assumptions that underlie the calculations of the above levels are presented in Tables I and II and associated text, infra.

A preferred mode of this invention is administration through inhalation, and to do so by incorporating the "active(s)" in an enclosed environment such as a room and, accordingly in the atmosphere around the occupant(s) of the enclosed environment. Such is accomplished, for example, by including an "active" in an air freshening composition. Accordingly, another measure for practice of this invention is inclusion of from about 1 up to about 125 micrograms per liter in the air of a room of the stress reactivity-reduction "active(s)" of our invention.

Reduction of physiological and/or subjective reactivity to stress resulting from practice of this invention is demonstrable objectively by means of a decrease in the systolic blood pressure of the human and subjectively in self-report of a significant increase in calmness and happiness and a significant decrease in embarrassment and anger under stress conditions.

The method by which the effect of the stress reactivity reducing substances of our invention has been ascertained is novel. This is the first method that uses a combination of psychological measurements, physiological measurements and a stressor to measure the effect of postulated stress reactivity-reducing substances taken alone or taken further together with ethyl alcohol and/or perfume compositions or perfumed articles or colognes on physiological and/or subjective reactivity to stress.

COMMENTARY (i) Modern medicine and much of aromatherapy alike are largely devoted to healing of the sick. The practice of this invention is directed to alleviation of physiological and/or subjective stress-induced reactivity in persons of a level not requiring the attention of the medical practitioners. Usually the reactivity to an ordinary stress situation (reactivity being measurable by a pulse-like elevation in systolic blood pressure) will not be accompanied by any untoward observable reaction.

As a result, although substances employed in practice of this invention are known to have physiologic activity, they are suggested in folk medicine and aromatherpy within a different use context than practice of this invention. For example, Valnet, supra, advises that nugmeg oil is an analgesic (when applied externally) and advises of internal (but not external) use for neroli oil. Tisserand, supra, advises that neroli oil makes a luxurious, relaxing and deodorant bath oil (which is in keeping with his report that neroli oil is one of the most effective sedative anti-depressant oils, and useful for insomnia, hysteria, states of anxiety and depression).

The aromatherapy and folk medicine literature, supra, cite the mode of administration as oral ingestion of gram quantities of material or application of gram quantities massaged over the body. None of the literature known to the inventors hereof suggests that inhalation or transdermal absorption of microgram quantities of the plant-derived substances or their synthetic counterparts (described in this invention) will reduce physiological and/or subjective reactivity to stress.

(ii) The results obtained through practice of this invention are comparable to results obtainable from meditation and biofeedback, including, notably, damping of the systolic blood pressure surges arising from stressful situations. However, unlike meditation or biofeedback, no training period is required in the use of the stress reactivity-reducing substances of our invention. The effect of the stress reactivity-reducing substances of our invention occurs within four minutes after inhalation of said substances.

(iii) Unlike anti-anxiety drugs, the effect of the volatile compositions of matter employed in the practice of our invention, (e.g., nutmeg oil, mace extract, neroli oil, valerian oil, myristicin, elemicin and/or isoelemicin) is prophylactic in nature, reducing (the physiological and/or subjective) reactivity to stress when stress conditions exist. Unstressed people do not respond to the method of this invention.

Thus, inclusion of actives in a bath oil composition does not fall within the practice of this invention for reason that bathing normally takes place sometime after occurrence of stressful situations. It is noted, however, that the relaxing effect attributed by Tisserand, supra, to neroli oil-containing bath oils may well be an effect on persons whose reactivity to stress does not subside for many hours.

(iv) Practice of this invention may be distinguished from the prior art employment of active essential oils, e.g., from nutmeg, in perfume compositions. Aside from generating presence of the actives in the surrounding atmosphere at a concentration less than is effective to reduce reactivity to stress, perfume usage in modern day practice involves employment during non-stress occurring situations.

EXPLANATION OF THE DRAWINGS

Figure 1:
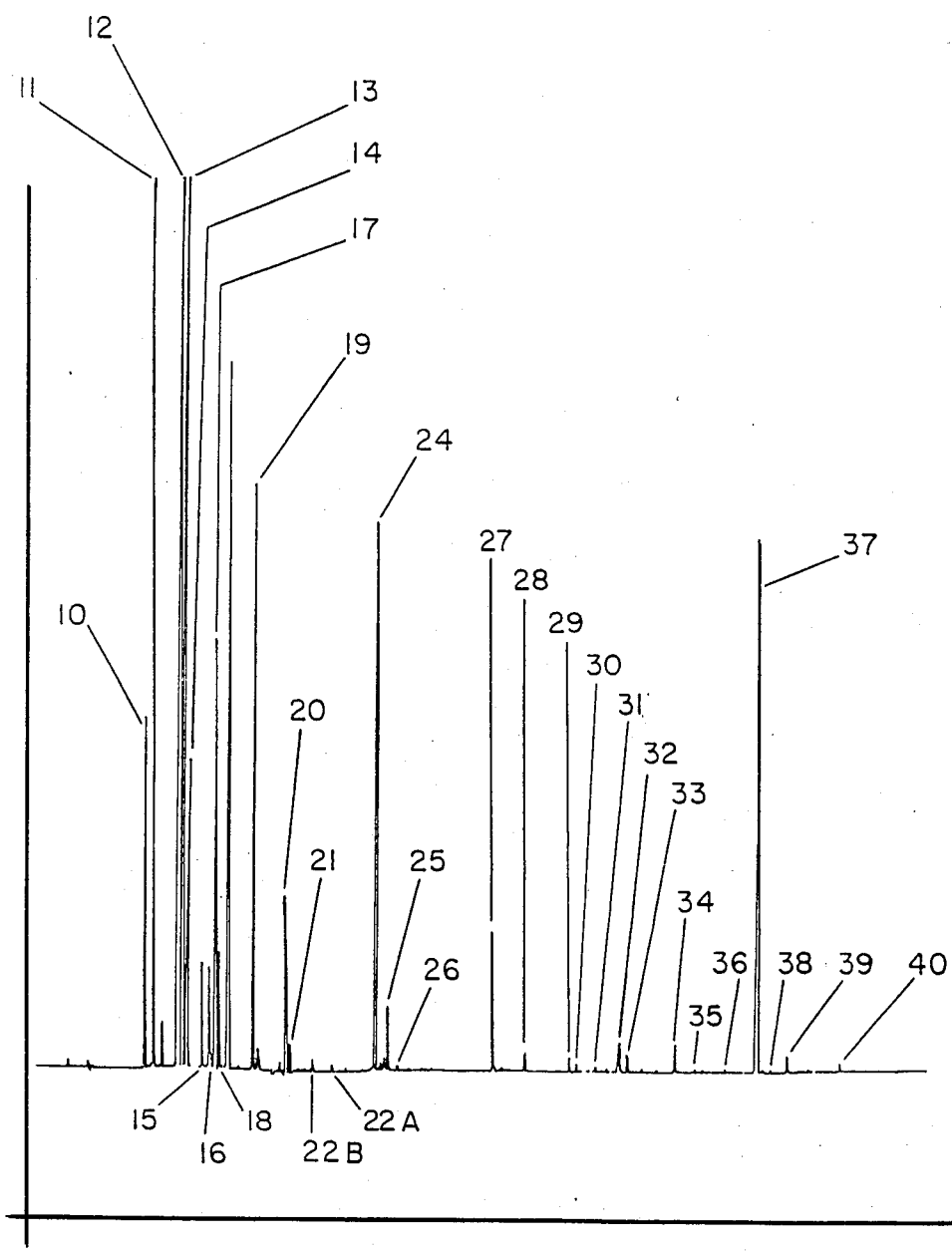
FIG. 1 is the GLC profile of the head-space above nutmeg oil measured according to the procedure of Example I(B) (Conditions: OV-1 fused silica column programmed at 75°–220° C. at 2° C. per minute). The nutmeg oil is East Indian Nutmeg Oil.

FIG. 1 is a GLC profile for the head-space above nutmeg oil East Indian as determined according to the procedure of Example I(B) (GLC Conditions: OV-1 fused silica column programmed at 75°–220° C. at 2° C. per minute).

The peak indicated by reference numeral 10 is the peak for α-thujene.

The peak indicated by reference numeral 11 is the peak for α-pinene.

The peak indicated by reference numeral 12 is the peak for sabinene.

The peak indicated by reference numeral 13 is the peak for β-pinene.

The peak indicated by reference numeral 14 is the peak for myrcene.

The peak indicated by reference numeral 15 is the peak for α-phellandrene.

The peak indicated by reference numeral 16 is the peak for Δ-3-carene.

The peak indicated by reference numeral 17 is the peak for α-terpinene.

The peak indicated by reference numeral 18 is the peak for p-cymene.

The peak indicated by reference numeral 19 is the peak for γ-terpinene.

The peak indicated by reference numeral 20 is the peak for terpinolene.

The peak indicated by reference numeral 21 is the peak for linalool.

The peaks indicated by reference numerals 22A and 22B are the peaks for 1-hydroxy-1-methyl-4-isopropyl-2-cyclohexane.

The peak indicated by reference numeral 23 is the peak for 2-methyl-5-ethyl furan.

The peak indicated by reference numeral 24 is the peak for 4-terpineol.

The peak indicated by reference numeral 25 is the peak for α-terpineol.

The peak indicated by reference numeral 26 is the peak for 1-methyl-3-hydroxy-4-isopropenyl benzene.

The peak indicated by reference numeral 27 is the peak for isobornyl acetate.

The peak indicated by reference numeral 28 is the peak for n-amyl methoxy benzenes.

The peak indicated by reference numeral 29 is the peak for eugenol.

The peak indicated by reference numeral 30 is the peak for α-terpinyl acetate.

The peak indicated by reference numeral 31 is the peak for α-cubebene.

The peak indicated by reference numeral 32 is the peak for eugenyl methyl ether.

The peak indicated by reference numeral 33 is the peak for α-copene.

The peak indicated by reference numeral 34 is the peak for trans-isoeugenol.

The peak indicated by reference numeral 35 is the peak for α-bergamotene.

The peak indicated by reference numeral 36 is the peak for 4-propenyl-1,2-dimethoxy benzene.

The peak indicated by reference numeral 37 is the peak for myristicin.

The peak indicated by reference numeral 38 is the peak for δ-cadinene.

The peak indicated by reference numeral 39 is the peak for elemicine.

The peak indicated by reference numeral 40 is the peak for 4-allyl-2,6-dimethoxy phenol.

Figure 3:
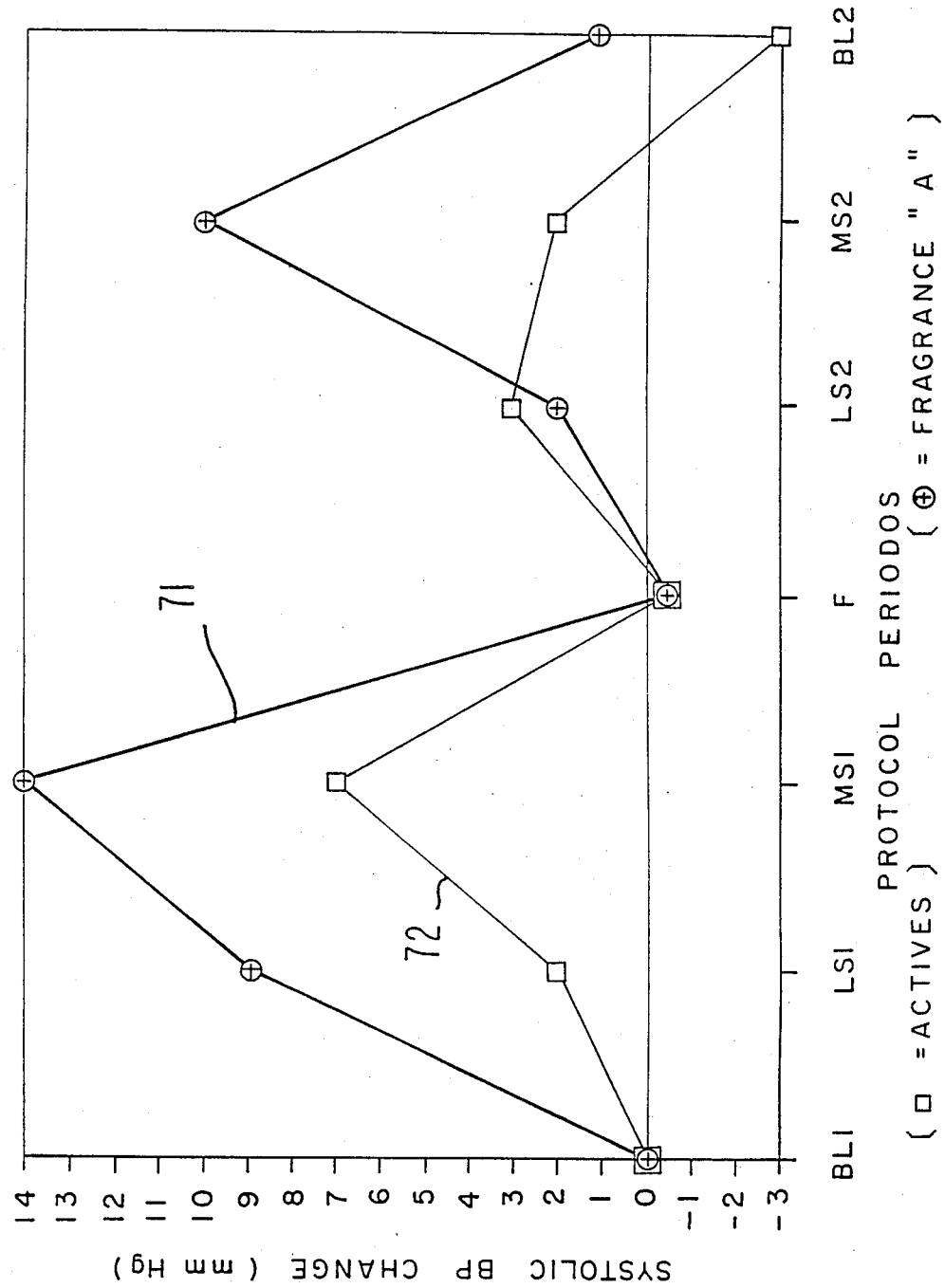
FIG. 3 is a graph showing systolic blood pressure change (mm/Hg) vs. protocol period for a composition of "actives" containing nutmeg oil, mace extract, neroli oil and valerian oil as well as for a composition containing a fragrance denoted as fragrance "A" (as described, infra) which does not contain any "actives". The "actives" of our invention cause the reduction of physiological and/or subjective reactivity to stress in a human. The means for determining the plots of data on the graph of FIG. 3 is set forth in Example III.

FIG. 3 sets forth the effect on blood pressure changes (of a human subject to stress conditions) of:
  (i) a composition of "actives" as set forth in Example II according to the protocol of Example III; and
  (ii) a fragrance composition entitled fragrance "A" specifically described according to Example II with the changes in blood pressure being in units of mm/Hg.

The graph indicated by reference numeral 71 is the graph of systolic blood pressure (mm/Hg) versus protocol period (e.g., BL1, LS1, MS1, F, LS2, MS2 and BL2) defined in Example II for fragrance "A"; that is, the fragrance that does not contain "actives", e.g., nutmeg oil, mace extract, neroli oil and valerian oil. The protocol periods are as follows:

BL1—baseline in "Stress I";
LS1—6 low stress questions in "Stress I";
MS1—6 mild stress questions in "Stress I";
F—two blood pressure points during application of fragrance "A" between "Stress I" and "Stress II";
LS2—6 low stress questions in "Stress II";
MS2—6 mild stress questions in "Stress II";
BL2—baseline at end of "Stress II".

The graph indicated by reference numeral 72 is the graph of systolic blood pressure (mm/Hg) versus protocol period when using the "actives" mixture, that is, the mixture of nutmeg oil, mace extract, neroli oil and valerian oil "actives composition" of Example II using the protocol of Example III. The meaning of each protocol period is as follows:

BL1—initial baseline for "Stress I";
LS1—6 low stress questions for "Stress I";
MS1—6 mild stress questions for "Stress I";
F—two blood pressure points during application of stress reactivity-reduction composition ("actives") after "Stress I";
LS2—6 low stress questions for "Stress II";
MS2—6 mild stress questions for "Stress II";
BL2—end baseline for "Stress II".

Figure 4:
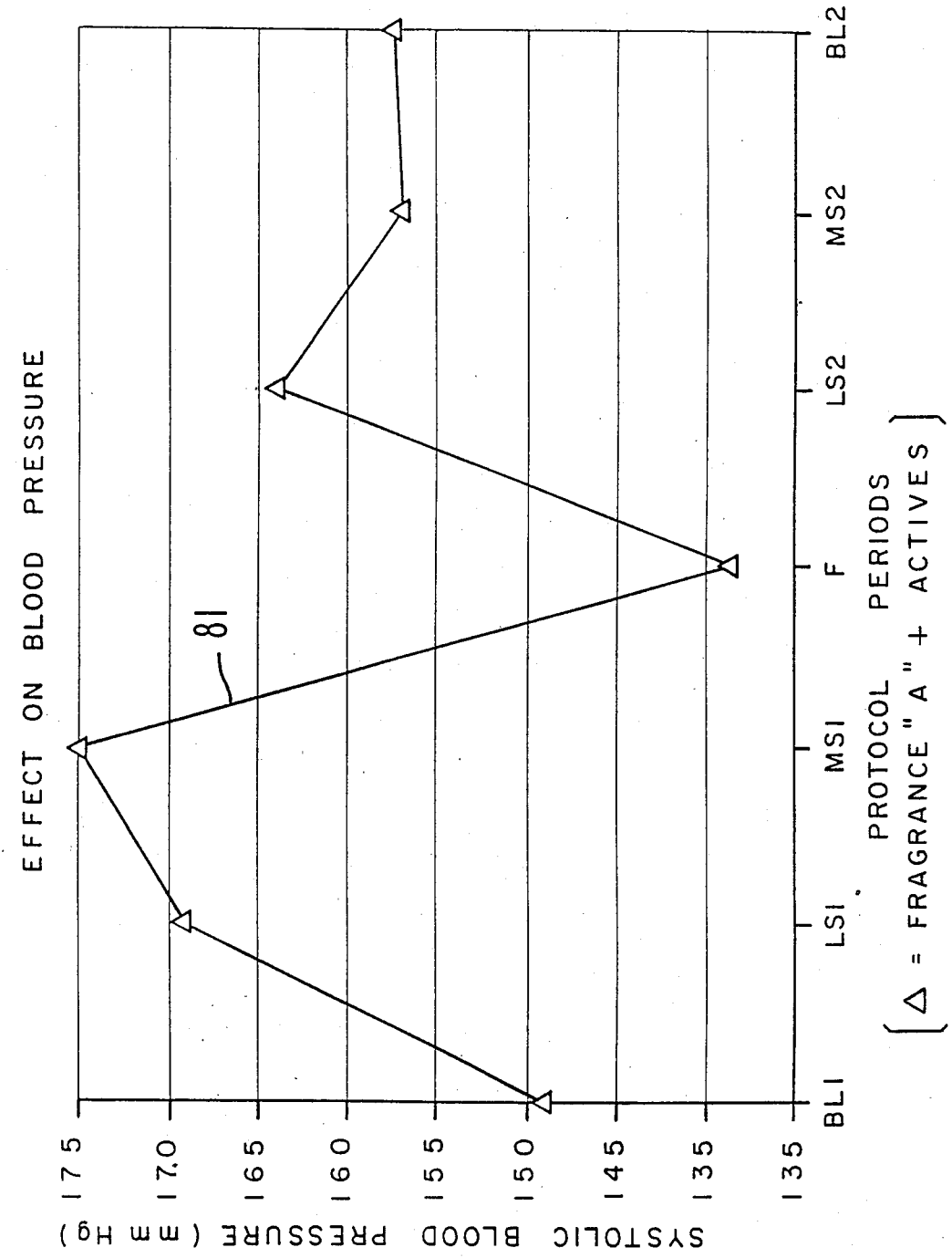
FIG. 4 is a graph showing systolic blood pressure (mm/Hg) vs. protocol period for a composition containing both (i) "actives" (containing nutmeg oil, mace extract, neroli oil and valerian oil) and, in addition, (ii) a composition denoted herein as fragrance "A" (as described, infra). The "actives" of our invention cause the reduction of physiological and/or subjective reactivity to stress in a human. The means for determining the plots of data on the graph of FIG. 4 is set forth in Example IV.

FIG. 4 sets forth the effect on blood pressure (of a human subject to stress conditions) of a composition of "actives" (as set forth in Example II) according to the protocol of Example III and in combination with a fragrance composition denoted as fragrance "A", with the blood pressure being in units of mm/Hg and with the measurements being made according to the procedure of Example IV.

The graph indicated by reference numeral 81 is the graph of systolic blood pressure (mm/Hg) vs. protocol period (e.g., BL1, LS1, MS1, F, LS2, MS2 and BL2) defined in Example IV for the combination: fragrance "A" and "actives", e.g., nutmeg oil, mace extract, neroli oil and valerian oil. The protocol periods are as follows:

BL1—baseline in "Stress I";
LS1—6 low stress questions in "Stress I";
MS1—6 mild stress questions in "Stress I";
F—two blood pressure points during application of the combination: fragrance "A" and "actives" between "Stress I" and "Stress II";
LS2—6 low stress questions in "Stress II";
MS2—6 mild stress questions in "Stress II";
BL2—baseline at end of "Stress II".

Figure 5:
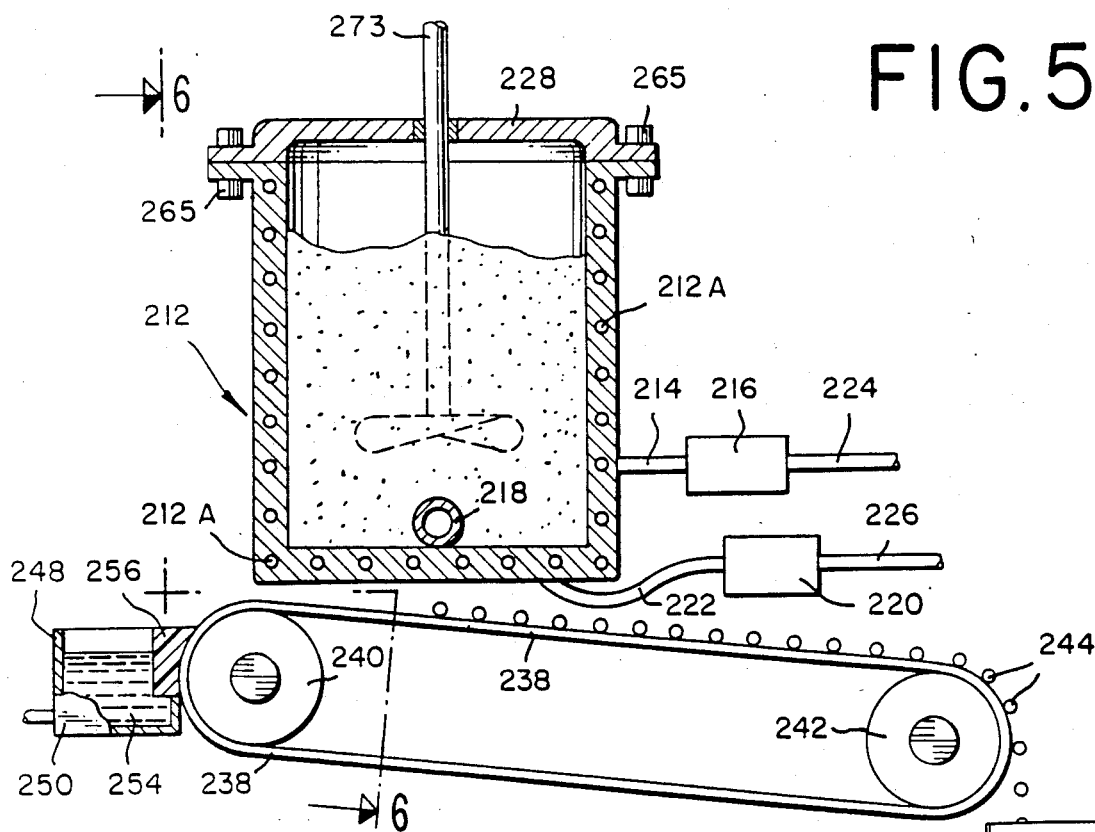
FIG. 5 is a cutaway side elevation view of apparatus used in preparing perfume-containing and stress reactivity-reducing substance-containing polymers of our invention.
Figure 6:
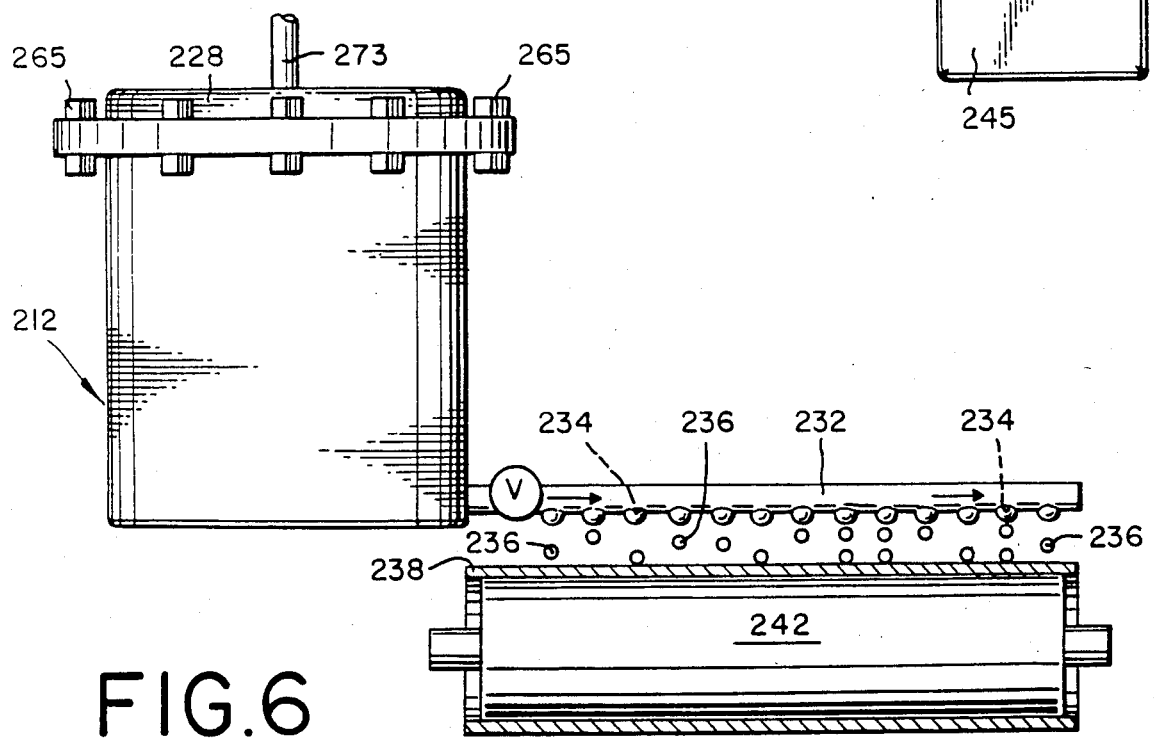
FIG. 6 is a cross sectional view taken along lines 6—6 of FIG. 5.

FIGS. 5 and 6 illustrates a preferred method for preparing compositions for the practice of our invention. A thermoplastic polymer, e.g., polyethylene, is heated to about 220°-250° F. in a container 212 of the kind illustrated in FIGS. 5 and 6. A formulation containing fragrance as well as stress reactivity-reduction "active(s)" (which includes one or a combination of the following:
Nutmeg oil;
Mace extract;
Neroli oil;
Valerian oil;
Myristicin;
Elemicin; and/or
Isoelemicin)
is then quickly added to the liquified thermoplastic polymer. The lid 228 is put in place and the agitating means 273 is actuated. The temperature is maintained at about 225° F. and the mixing is continued for about 5-15 minutes. The valve "V" is then opened to allow flow of the molten thermoplastic polymer enriched with fragrance and "active" substance containing one or a combination of:
Nutmeg oil;
Neroli oil;
Valerian oil;
Mace extract;
Myristicin;
Elemicin; and/or
Isoelemicin
to exit through the orifices 234. The liquid falling through the orifices 234 solidifies almost instantaneously upon impact with moving cooled conveyor 238. The thermoplastic polymer beads or pellets 224 having pronounced physiological and/or subjective reactivity reduction (to stress) effects are thus formed.

The conveyor 238 is moved using conveyor rollers 240 and 242. The vessel 212 is heated using heating coils 212A powered using power input supplies indicated by reference numerals 214, 216, 224, 222, 220 and 226. The solidified beads containing stress reactivity reduction "active(s)" are indicated by 244 traveling into container 245 where they are used for subsequent processing. The conveyor is cooled using a cooling device indicated by reference numerals 248, 256, 250 and 254.

DETAILED DESCRIPTION OF THE INVENTION

Our invention necessarily also involves a method for detecting physiological and/or subjective reactivity to stress in a human comprising testing a human likely to exhibit physiological and/or subjective reactivity by:

(i) measuring the initial blood pressure and mood of said human; then
(ii) administering stress to said human by means of application of a stressor;
(iii) simultaneously measuring blood pressure change and mood change resulting from the application of said stress to said human; thereafter
(iv) administering a postulated stress reactivity-reducing substance to said human; and
(v) simultaneously measuring the blood pressure change and mood change in said human resulting from the application of said postulated stress reactivity-reducing substance during the application of said stressor to said human.

As has already been pointed out, our invention is directed to a method for causing the reduction of physiological and/or subjective reactivity to stress in a human being subjected to stress conditions which comprises administering to said human an effective amount of a substance which may be one or a mixture of:
Nutmeg oil;
Mace extract;
Neroli oil;
Valerian oil;
Myristicin having the structure:

Elemicin having the structure:

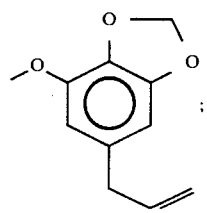

and/or
Isoelemicin having the structure:

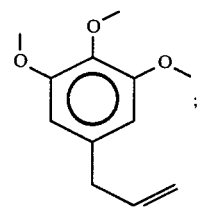

taken alone or taken further together with a carrier which may be a perfumed article or cologne and/or ethanol.

Insofar as the nutmeg oil, mace extract, neroli oil and valerian oil are concerned, the various varieties of such materials are useful in the practice of our invention. Thus, for example, Nutmeg Oil East Indian or Nutmeg Oil West Indian are useful in the practice of our invention. Standard commercial mace extract is useful in our invention as is the more highly purified form thereof. Commercial valerian oil is useful in the practice of our invention as is the refined version, doubly distilled valerian oil.

In addition, naturally occurring or synthetically produced myristicin, elemicin and isoelemicin are useful in the practice of our invention.

Thus, myristicin having the structure:

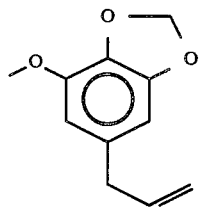

may be isolated as by distillation from Nutmeg Oil East Indian or West Indian or Nutmeg Oil Fiji or it may be synthesized according to the reaction sequence:

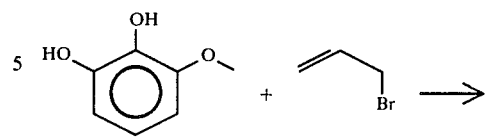

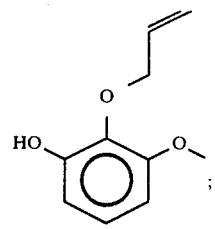

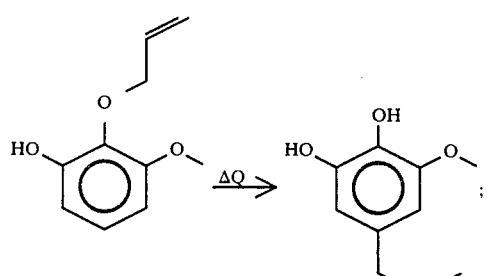

and

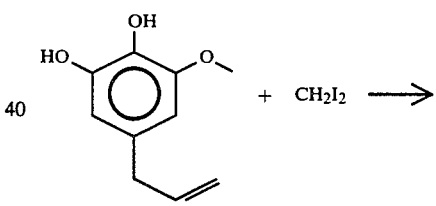

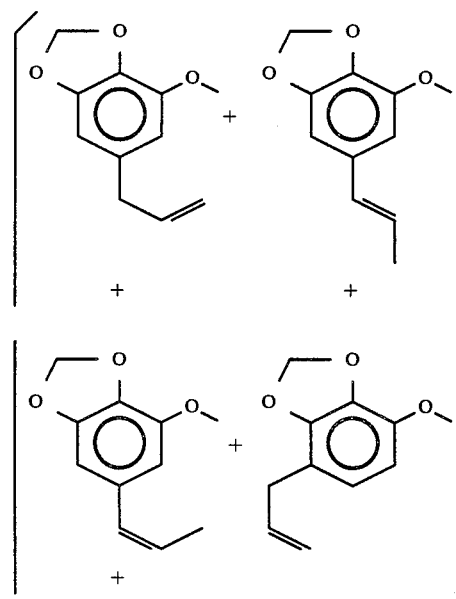

-continued

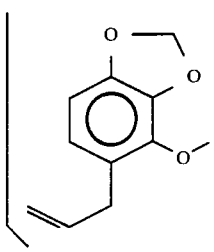

Thus, our invention is directed to the use of one or a mixture of the following ingredients:
Nutmeg Oil;
Mace Extract;
Valerian Oil;
Neroli Oil;
Myristicin;
Elemicin; and/or
Isoelemicin,
which ingredients, i.e., the "active(s)", may be administered alone or further together with a "non-active" carrier composition (such as (i) ethanol or (ii) a carrier perfume composition or (iii) a carrier perfumed article) for the reduction of physiologic change and/or subjective manifestations of reactivity in a human being subjected to stress conditions. This reduction in reactivity decreases the systolic blood pressure surges caused by stress and generates a significant increase in calmness and happiness and a significant decrease in embarrassment and anger in said human. The physiological change and subjective manifestations of reactivity to stress and a reduction of reactivity to "stress" are quantifiable, see Examples II, III, IV and V, infra.

To repeat, the "active" stress reactivity-reducing substances of our invention, to wit:
Neroli Oil;
Mace Extract;
Nutmeg Oil;
Valerian Oil;
Myristicin;
Elemicin; and
Isoelemicin
are, in their own right, perfumery substances known in the prior art. For example, myristicin having the structure:

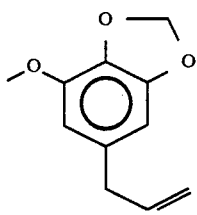

contributes an interesting spicy aroma to perfumes.

However, the terms "carrier perfume" and "carrier perfume composition" are used herein, within an inert carrier context to means mixtures of organic compounds (other than such "actives") including, for example, fragrant alcohols, fragrant aldehydes such as, for example, the aldehyde having the structure:

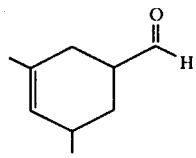

ketones, nitriles, ethers such as, for example, the cyclic ether having the structure:

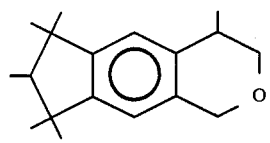

and the cyclic ether having the structure:

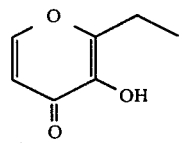

(but excluding, of course, elemicin, isoelemicin and myristicin), and such materials as lactones, hydrocarbons, synthetic essential oils and natural essential oils (excluding, of course, the natural essential oils: nutmeg oil, valerian oil, neroli oil and mace extract) in admixture so that the combined odors of the individual components produce a pleasant or desired fragrance.

Although state of the art perfume and cologne compositions are contemplated for carrier purposes in practice of this invention, the "actives" are fragrances, and therefore some comments here about perfumery practices are warranted.

Perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling fresh smelling materials.

In perfume compositions, each individual component will contribute its particular olfactory characteristics but the overall effect of the perfume composition will be the sum of the effects of each ingredient. Thus, individual perfumery compounds or mixtures thereof can be used to alter the aroma characteristics of a proposed perfume composition, for example, by highlighting or moderating the olfactory reaction contributed by another ingredient in the composition. The "actives" of this invention will alter the aroma characteristics of a carrier perfume composition in addition to causing stress reactivity reduction in a human who is subjected to stress conditions. Therefore the aroma desired for the composition as a whole, rather than the aroma of the carrier perfume formulation alone, should be made the basis upon which the carrier perfume composition is formulated.

It should be appreciated that a perfume or cologne composition containing "actives" is being administered by inhalation, and, to the extent the composition has been applied to the skin, transdermally as well. Air freshener compositions are administered almost entirely through inhalation.

The amount of the stress reactivity reduction perfume composition required for effective action (with regard to the user) depends on many factors including the skin condition of the user; the environmental conditions during the period of desired effectiveness (e.g., humidity, temperature and pressure), the emotional state of the user at the point in time of application; the physical characteristics of the user including body weight and base line systolic blood pressure at the point(s) in time of application(s). All of which is to say that individual reactivity and feelings of comfort by a user will determine the amount effective for that user.

The perfume composition may be used "as is" (e.g., 100%) or in a "cologne". Directions for quantity to use and frequency of use, as well as variations in the formulation, e.g., summer and winter formulations, may be employed to assure that effective levels of the "actives" may be administered. For the purpose of this invention, the term "cologne", as exemplified hereinafter, means a perfume composition incorporated in an alcoholic or hydroalcoholic solution. The perfume composition can vary between 1 to 99% and the balance of the formulation is comprised of alcohol or a mixture of water and alcohol. The water:alcohol weight ratio can vary from 50:50 to 0:100. Examples of alcohols typically used in these products are SDA 39-C and SDA-40, either 190 "proof" or anhydrous (See "Ethyl Alcohol Handbook", 5th Edition, Published by National Distillers and Chemical Co.). The cologne composition can also contain solubilizing agents, emollients, humectants, thickening agents, bacteriostats or other cosmetically-used ingredients.

Although perfume compositions and colognes would normally be considered to administer the "actives" by inhalation or smelling, placement thereof on the epidermal skin tissue generates, also, transdermal penetrative administration.

Perfumery materials which are compatible with the stress reactivity reduction substances have been employed in aromatizing carrier perfumed articles. Such perfumed articles include fabric softener compositions, dryer-added fabric softener articles, e.g., BOUNCE ® (a Registered Trademark of the Procter & Gamble Company of Cincinnati, Ohio), cosmetic powders, talcs, solid or liquid anionic, cationic, nonionic or zwitterionic detergents and perfumed polymers as well as deodorant sticks, hair preparations and bar soaps as exemplified, infra. Furthermore, perfume materials which are compatible with the stress reactivity-reducing substances of our invention have been employed in air fresheners. Thus, a great number of state-of-the-art perfume compositions and perfumed articles are available for use as the non-active carrier (perfumed) composition and (perfumed) articles within which the "actives" may be incorporated for practice of this invention.

Thus, the stress reactivity-reducing substances can be used alone or taken together with carrier perfume compositions alone or through carrier perfumed articles. Many well known articles of commerce may be the carrier such as solid or liquid anionic, cationic, nonionic or zwitterionic detergents bar soaps, space odorants and deodorants; colognes, toilet waters, hair preparations, such as lacquers, brilliantines, and pomades; cosmetic preparations, such as creams, deodorants, hand lotions and sun screens; and powders, such as talcs, dusting powders, face powders and the like. When perfume compositions are used as an olfactory component of a perfumed article, such as a solid or liquid anionic, cationic, nonionic or zwitterionic detergent or a cosmetic powder or a deodorant stick, as little as 0.1% by weight of the overall perfume and stress reactivity-reducing "active(s)" (in combination) in the perfumed article will suffice. In space odorant applications, on the other hand, as much as 99% of the combine carrier perfume substance and stress reactivity-reducing substance can be present. Thus, perfumed articles may contain in the range of from about 0.1% up to about 99% of a composition of matter consisting essentially of the stress reactivity-reducing "active(s)" and "non-active" carrier perfume substance.

It is interesting to note that when a stress reactivity-reducing "active" is used in a deodorant stick or deodorant bar soaps to practice our invention, a twofold effect takes place:
 (i) the deodorant stick itself acts as a "deodorant" in the axillary area of the human being; and
 (ii) the stress reactivity-reducing "active(s)" is administere by inhalation or transdermally to cause reduction in physiological and/or subjective reactivity to stress in those individuals subjected to stress conditions thereby giving rise to a double efficacious reduction in "malodor" evolved from the axillary regions of such human to the surrounding environment.

The term "perfumed article" also includes solid-form polymers, such as polyethylene, polypropylene and other polymers which contain pores within which are occluded a carrier perfume composition combined with the stress reactivity-reducing "active(s)". Such perfumed polymers can be produced as described herein or according to any technique well known to one having ordinary skill in the art.

In addition, the stress reactivity-reducing substances of our invention, e.g., neroli oil, nutmeg oil, mace extract, valerian oil, myristicin, elemicin and isoelemicin taken alone or taken in combination may, by themselves, be absorbed into the interstices of microporous or macroporous polymers. Furthermore, like carriers of materials other than synthetic polymers can be used to generate a "perfume article" such as a gum (e.g., guar gum, xanthan gum, or gum arabic) or an encapsulating composition such as a gelatin (as by coacervation) or such as a urea/formaldehyde prepolymer to form a urea/formaldehyde polymeric wall around a liquid center, which liquid center contains the stress reactivity-reducing "active(s)" alone in conjunction with ethanol and/or a carrier perfume composition.

Unlike anti-anxiety drugs, as mentioned supra, the effect of the "actives" materials is to reduce the physiological and/or subjective reactivity to stress in a person who is subjected to stress conditions. Individuals who are not being subjected to stress conditions do not react to the administration of any of the above-mentioned "active(s)" according to the practice of this invention.

Unlike meditation or biofeedback, no training period is required for the human who is to be treated in order to effect reduction of physiological and/or subjective reactivity to stress. The effect(s) of an "active" material, e.g., nutmeg oil, mace extract, neroli oil, valerian oil, myristicin, elemicin and isoelemicin, occurs within four minutes after initial inhalation or smelling of the substance by the individual under stress to whom the substance is administered.

The weight ratio of stress reactivity-reducing "active(s)" to the ingredients in the carrier perfume composition, cologne or the perfumant applied to generate the carrier perfumed article is in the range of from about 1:100 up to about 100:1. Is is emphasized that the carrier perfume composition, cologne and perfumant applied to generate the carrier perfumed article do not otherwise contain any other stress-reactivity reducing substances, or for that matter any stress-affecting or hypotensive substances employed in the medical arts, for example, benzodiazepine derivatives for anxiety and methyldopa or propranolol for hypertension.

Our invention expressly contemplates the use of ethyl alcohol in conjunction with the "actives". The ethyl alcohol may enhance the efficacy of the "actives". As has already been pointed out ethyl alcohol is a major component in standard cologne compositions.

When the stress reactivity-reducing "active(s)" is used in conjunction with ethyl alcohol, the weight ratio of "active(s)" to the ethyl alcohol (based upon pure ethanol) is in the range of from about 1:99 up to about 99:1. The ethanol used in conjunction with practice of our invention may vary from 50% aqueous ethanol up to 100% (absolute ethanol).

One great advantage of the practice of this invention for the reduction of physiological and/or subjective reactivity to stress in humans is the fact that the dose level of "active(s)" is miniscule; being of the order of micrograms.

Specifically with regard to dose levels, the "actives" are to be divided into two groups:

Group "ALEPH"

Nutmeg oil;
Mace extract;
Neroli oil; and
Valerian oil
(taken alone or in combination)

Group "BETH"

Myristicin;
Elemicin; and
Isoelemicin
(taken alone or in combination).

The group "ALEPH" dose for the purpose of our invention is from about 13 micrograms up to about 1000 micrograms. The group "BETH" dose for the purpose of our invention is from about 0.013 micrograms up to about 50 micrograms.

When materials from the Groups "ALEPH" and "BETH" are used in combination, the dosage of "actives" is from about 0.013 micrograms up to about 1000 micrograms with an upper limit of the Group "BETH" component within said combination being about 50 micrograms.

One of the preferred modes of this invention is administration of the stress reactivity-reducing composition by incorporating the "active(s)" in the environment surrounding the user. Such is accomplished, for example, by including "active(s)" in the air freshening composition. Accordingly, another measure for practice of this invention is inclusion of from about 1 up to about 125 micrograms per liter of stress reactivity-reducing "active" in the air of a room. Preferably, a group "ALEPH" "active" is used for this purpose.

Reverting to "active(s)" dosage ranges in general, at the upper bound of the ratio of weight of a carrier perfume composition (containing no "actives"):weight of "active" Group "ALEPH" (that is, 100:1), the total amount of perfume composition used requires a range of from about 13 micrograms up to about 1000 micrograms "active" and thus requires a range of from about 1300 micrograms (1.3 mg) up to about 100,000 micrograms (0.1 gm) of non-active-containing carrier perfume composition. Furthermore, at the upper bound of the ratio of weight of perfume composition (containing no "actives"):weight of "active" Group "BETH" (that is, 100:1), the total amount of perfume composition used contains a range of from about 0.013 micrograms up to about 50 micrograms "actives" and thus constitutes a range of from about 1.3 micrograms up to about 5000 micrograms (5 mg) of non-active-containing carrier perfume composition.

By the same token, at the lower limit of the ratio of weight of a carrier perfume composition (containing no "actives"): weight of "active" Group "ALEPH" (that is, 1:100), the total amount of perfume composition requires a range of from about 13 micrograms up to about 1000 micrograms "actives" and thus requires a range of from about 0.13 micrograms up to about 10 micrograms of non-active-containing perfume composition. At the said lower limit, the ratio of weight of perfume composition (containing no "actives"):weight of "active" Group "BETH" (that is, 1:100), the total amount of perfume composition used nonetheless contains a range of from about 0.013 micrograms up to about 50 micrograms "actives" and thus constitutes a range of from about 0.00013 micrograms up to about 0.50 micrograms of non-active carrier perfume composition. Thus, the working ranges of perfume+"active") compositions contemplated within the scope of the invention vary as follows:

(a) For Group "ALEPH" "actives"—from 13 micrograms up to 100,000 micrograms (0.1 grams); and
(b) For Group "BETH" "actives"—from 0.013 micrograms up to 5000 micrograms (5 mg).

As previously stated, perfumed articles contemplated within the scope of this invention may contain in the range of from 0.1% up to 99% by weight of combined non-active carrier perfume and "active(s)". Also, as previously stated, the weight ratio of carrier perfume: "active(s)" may vary from about 1:100 up to 100:1.

It therefore follows that 100 grams of a perfumed article employed in practice of our invention will contain from about 0.1 grams up to about 99.0 grams of a perfume composition that includes "active(s)".

It follows also that practical restraints exist upon practice of this invention through perfumed articles. For example, when administration of "actives" from perfumed garments is desired, transfer of "actives" to the garments from perfumed detergent may not be practical. However, transfer from a perfumed fabric softener to the fabric is more feasible. More often than not practical restraints simply challenege the skill of the formulator when administration is sought from perfumed deodorant compositions, cosmetic powders, hand soaps, and the like, for example. Some perfumed articles offer less of a challenge to the formulator, or no challenge at all; air freshener compositions, for example. The range of 0.1-99.0 gms of perfume composition per 100 grams of article should be considered guidelines rather than strict limits.

Some uncertainty is acknowledged also for the administration range of 13-1000 micrograms of "ALEPH" group "active(s)" and 0.013-50 micrograms of "BETH" group "active(s)". The experimental effort underlying this invention may not translate exactly to the dosage range suited to large scale practice of this invention, for (necessarily) having been conducted under artificial conditions. For better understanding of this invention, and as aid to translation of the exemplary material herein into large scale practice of the invention, details of the experimental conditions and dosage assumptions made by the inventor hereof are now provided.

In specific, the effective dose levels for Groups "ALEPH" and "BETH" set forth above constitute estimates of quantities breathed in and effectively taken up by the subjects from a perfumer's blotter as described in Example II, infra, or from a wick-vial arrangement as described in Examples III and IV, infra.

The source of the stress reactivity reduction composition was about 1.5 inches from the subject's nose. For the estimation of dosages, the following assumptions were used:

1. Breathing rate for an average subject at rest is 10 liters per minute.
2. The total amount of substance breathed in and retained is 25% of the material that is evaporating. We assumed intake of 50% of the material evaporating from the source. Of the material breathed in, 50% was subsequently exhaled.
3. The total amount of the substance effectively taken up by the body is about 10% of the breathed in and retained substance.
4. The average body weight of a human being is 65 kg.

The assumptions used for estimation of dosages were based on measured plasma levels for $\Delta^9$-tetrahydrocannabinol ($\Delta^9$THC) that had been administered by inhalation of marihuana smoke. For this situation 50% of the $\Delta^9$-THC breathed in was retained and approximately 10% of the retained material was found in the plasma. (Nahas, G. and Paton, D., eds., "Marihuana: Biological Effects,", in Advances in the Biosciences, Vols. 22/23, Pergamon Press, N.Y., [1979], page 289.) In addition to the above assumptions, the following parameters were measured:

1. The amount of substance evaporating from the source of postulated stress reactivity-reduction composition was obtained by weight loss measurements.
2. The concentration of Group "BETH" component(s), e.g., Myristicin, Elemicin and Isoelemicin in the head-space was measured by gas chromatography.
3. The total time that the subject breathed the stress reactivity-reduction substances was 20 minutes.

The following Tables I and II present a summary of our results.

TABLE I

Evaporation Rates for Stress Reactivity Substance and Non-Active-Perfume Containing Substance

| Example | Evaporation Rate (mg/min) Oil Containing Actives and Non-Active-Containing-Perfume Composition | Ethyl Alcohol | % Actives | Calculated Evaporation Rate Group "ALEPH" Component (mg/min) (a) | Amount of Group "BETH" Component in Group "ALEPH" Component Being Evaluated (micrograms/min) (b) |
|---|---|---|---|---|---|
| II | 0.12 | 0.18 | 40 | 0.05 | 0.05 |
| III | 0.26 | 0.26 | 100 | 0.26 | 0.26 |
| IV | 0.15 | — | 40 | 0.06 | 0.06 |
| Fragrance B | 0.26 | 0.26 | 2 | 0.005 | 0.005 |

Notes:
(a) The calculated evaporation rate of the Group "ALEPH" component is the evaporation rate of the oil-containing "actives" × the percent "actives" in the oil.
(b) The amount of Group "BETH" component in Group "ALEPH" was determined by gas chromotography (see Example I) to be approximately 0.1% of the "ALEPH" concentrations.

TABLE II

Concentrations Breathed in and Retained and Concentrations Absorbed

| Example | Amount Breathed in and Retained (micrograms/min) | Assumed Amount Group "ALEPH" Component absorbed into Bloodstream (micrograms/min) | Amount Group "BETH" Component (Part of Group "ALEPH" Component Absorbed (micrograms/min) |
|---|---|---|---|
| II | 13 | 1.3 | 0.0013 |
| III | 65 | 6.5 | 0.0065 |
| IV | 15 | 1.5 | 0.0015 |
| Fragrance B | 1.3 | 0.13 | 0.00013 |

TABLE III

Suggested Levels Compositions

1. Concentrations in Air Space:
Assume amount breathed in/breathing rate. [This is equal to the evaporation rate for "ALEPH" or "BETH" by two to correct for the amount not breathed in, divided by the breathing rate which is assumed to be 10 liters

| | Apparent Amount in Air Space Stress Reactivity Reduction Substance (Micrograms per liter) | |
|---|---|---|
| Example | Group "ALEPH" Component | Group "BETH" Component Contained in Group "ALEPH" Component |
| II | 2.50 | 0.00250 |
| III | 13.00 | 0.01300 |
| IV | 3.00 | 0.0030 |
| Fragrance B* | 0.25 | 0.00025 |

2. Dose Levels. Minimum Dose Level is Amount Effectively Absorbed for Example II × 10 min.
Minimum = 13 micrograms of Group "ALEPH" Component and 0.013 micrograms of Group "BETH" component

TABLE III-continued

Maximum dose level is estimated from folk medicine literature suggestions for soothing bath oil and other external uses for the actives. Parenthetically, it is noted that the maximum dose level is estimated to be about 1% or less of the quantities reported to have stupefacient activity.

*Fragrance B is a prior art perfume composition containing nutmeg oil. This fragrance was evaluated for reason that it contains the highest level of any actives in the perfumes known to the inventors hereof. The quantity of actives administered is about 10% of the minimum dose level for practice of this invention.

Although the experimental data is limited to administration through inhalation which treatment mode involves transport of "actives" across internal body membranes, the "active(s)" are known to transport across internal body membranes, notably across epidermal tissue (see, for example, disclosures of external application of "actives" in folk medicine and aromatherapy arts). Practice of this invention includes, then, both transdermal administration, and through inhalation with, it is believed, the same dosage range for treatment by either treatment mode.

The following Examples II, III, IV and V set forth processes for preparing and testing stress reactivity-reducing compositions of our invention. Examples following Example V, e.g., Example VI, et seq, set forth incorporation of the stress reactivity-reducing substances in perfumed articles.

The following Example I sets forth methods for analyzing and producing certain of the stress reactivity-reducing substances e.g., myristicin and elemicin and the like.

It is to be understood that the invention is not to be so limited to the embodiments herein exemplified.

EXAMPLE I(A)

Isolation of Myristicin from East Indian Nutmeg Oil and Head Space Analysis of East Indian Nutmeg Oil East Indian Nugmeg Oil was carefully distilled on a 1 plate short path column yielding the following fractions:

| FRACTION NO. | VAPOR TEMP. (°C.) | LIQUID TEMP. (°C.) | VACUUM psia | WEIGHT OF FRACTION (gms) |
|---|---|---|---|---|
| 1 | 43/42 | 47/46 | 20/20 | 26.2 |
| 2 | 42 | 47 | 20.0 | 77.6 |
| 3 | 43 | 48 | 20.0 | 73.1 |
| 4 | 45 | 52 | 20.0 | 67.0 |
| 5 | 45 | 52 | 20.0 | 84.0 |
| 6 | 45 | 54 | 20.0 | 67.6 |
| 7 | 47 | 63 | 20.0 | 58.4 |
| 8 | 49 | 76 | 20.0 | 62.5 |
| 9 | 63 | 82 | 5.0 | 38.4 |
| 10 | 71 | 100 | 1.2 | 45.0 |
| 11 | 94 | 108 | 1.2 | 14.3 |
| 12 | 98 | 111 | 1.2 | 24.6 |
| 13 | 100 | 117 | 1.2 | 26.9 |
| 14 | 96 | 130 | 1.1 | 17.9 |
| 15 | 100 | 180 | 1.0 | 10.5 |

Fractions 13 and 14 were bulked and further purified by means of distillation on a spinning band distillation column (Nester Faust Auto Annular Distillation Unit) yielding the following fractions:

| FRACTION NO. | VAPOR TEMP. (°C.) | LIQUID TEMP. (°C.) | VACCUUM mm/Hg PRESSURE | WEIGHT OF FRACTION (gms) |
|---|---|---|---|---|
| 1 | 68/72 | 156/158 | 0.6/0.6 | 1.7 |
| 2 | 72 | 161 | 0.60 | 2.9 |
| 3 | 74 | 161 | 0.60 | 3.6 |
| 4 | 72 | 158 | 0.60 | 4.2 |
| 5 | 70 | 156 | 0.60 | 3.5 |
| 6 | 74 | 157 | 0.65 | 3.2 |
| 7 | 71 | 159 | 0.50 | 4.2 |
| 8 | 71 | 160 | 0.55 | 4.9 |
| 9 | 71 | 159 | 0.55 | 3.6 |
| 10 | 71 | 161 | 0.55 | 2.5 |
| 11 | 71 | 169 | 0.55 | 2.5 |
| 12 | 66 | 185 | 0.55 | 1.7 |

Fractions 7–12 are bulked.

FIG. 1 is the GLC profile for bulked fractions 7–12 of the foregoing distillation (Conditions: 400'×0.032" fused silica/carbowax column programmed at 75°–220° C. at 2° C. per minute).

The thus-produced substantially pure myristicin was used for further experiments as set forth in Examples II, et seq.

EXAMPLE I(B)

Head Space Analysis of Nugmeg Oil and Mace Oil

2 Grams of Nutmeg Oil East Indian or Mace Oil was placed in a 250 cc single neck receiver. The receiver was fitted with a rubber stopper into which was embedded a stainless steel hook. On the hook was placed a 2 $cm^2$ stainless steel screen impregnated with dioctylphthalate. The dioctylphthalate absorbed the ingredients of the head space above the nutmeg oil for a period of 15 minutes. At the end of the 15 minute period, the stopper with the screen was removed from the flask and the screen was removed from the hook. The screen was then placed in a small clinical centerfuge and the dioctylphthalate containing the ingredients of the head space was separated from the screen by means of centrifugation. The resulting product was then subjected to GLC analysis (Conditions: OV-1 fused silica column programmed at 75°–220° C. at 2° C. per minute).

Figure 2:
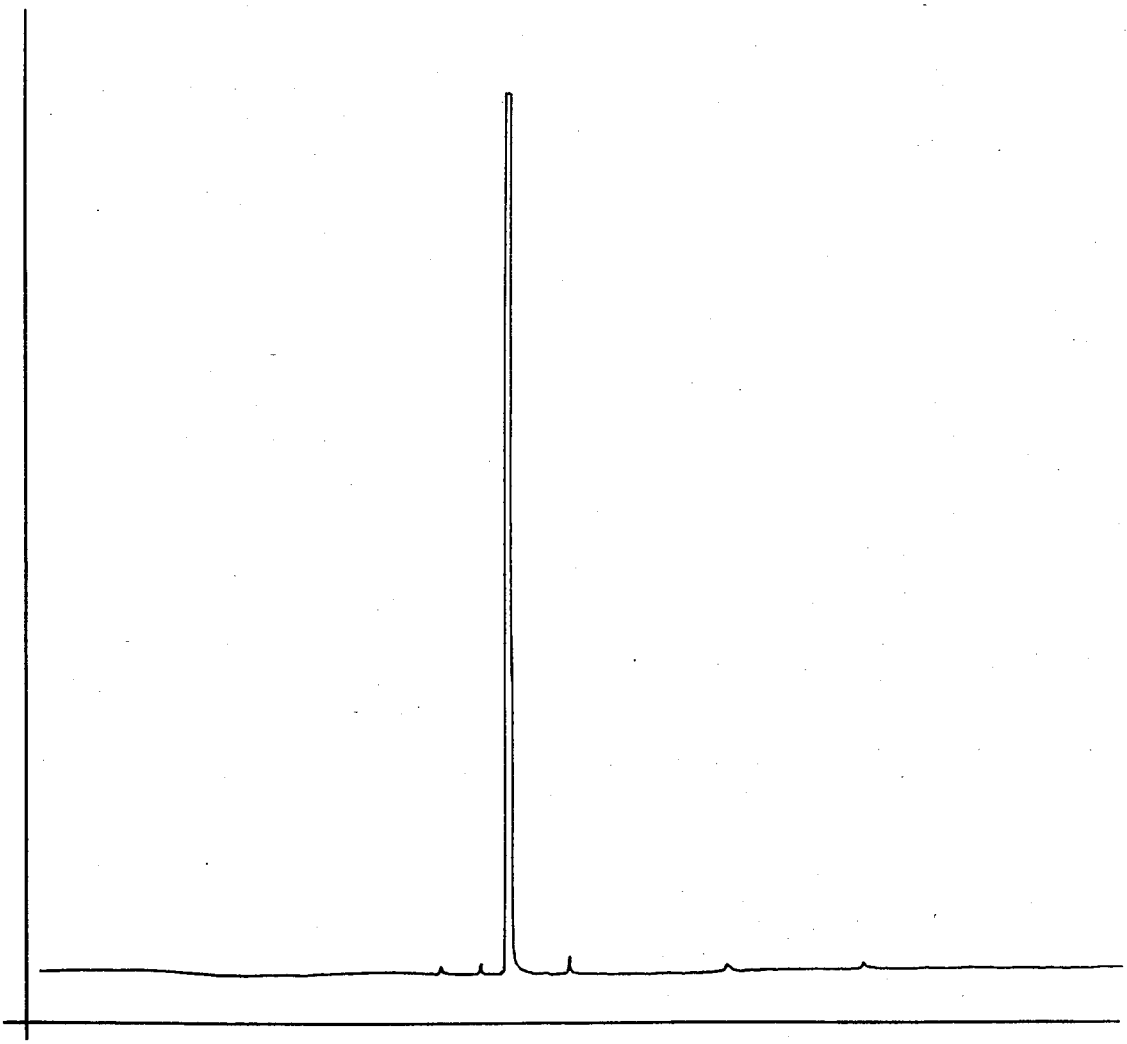
FIG. 2 is the GLC profile for bulked fractions 7–12 of the second distillation of nutmeg oil East Indian according to the procedure of Example I(A) (Conditions: 400′×0.032″ carbowax/fused silica column programmed at 75°–220° C. at 2° C. per minute).

FIG. 2 is the GLC profile for the head space above the nutmeg Oil.

The peak indicated by reference numeral 10 is the peak for α-thujene.

The peak indicated by reference numeral 11 is the peak for α-pinene.

The peak indicated by reference numeral 12 is the peak for sabinene.

The peak indicated by reference numeral 13 is the peak for β-pinene.

The peak indicated by reference numeral 14 is the peak for myrcene.

The peak indicated by reference numeral 15 is the peak for α-phellandrene.

The peak indicated by reference numeral 16 is the peak for δ-3-carene.

The peak indicated by reference numeral 17 is the peak for α-terpinene.

The peak indicated by reference numeral 18 is the peak for p-cymene.

The peak indicated by reference numeral 19 is the peak for γ-terpinene.

The peak indicated by reference numeral 29 is the peak for terpinolene.

The peak indicated by reference numeral 21 is the peak for linalool.

The peaks indicated by reference numerals 22A and 22B are the peaks for 1-hydroxy-1-methyl-4-isopropyl-2-cyclohexene.

The peak indicated by reference numeral 23 is the peak for 2-methyl-5-ethyl furan.

The peak indicated by reference numeral 24 is the peak for 4-terpineol.

The peak indicated by reference numeral 25 is the peak for α-terpineol.

The peak indicated by reference numeral 26 is the peak for 1-methyl-3-hydroxy-4-isopropyl benzene.

The peak indicated by reference numeral 27 is the peak for isobornyl acetate.

The peak indicated by reference numeral 28 is the peak for n-amyl methoxy benzenes.

The peak indicated by reference numeral 29 is the peak for eugenol.

The peak indicated by reference numeral 30 is the peak for α-terpinyl acetate.

The peak indicated by reference numeral 31 is the peak for α-cubebene.

The peak indicated by reference numeral 32 is the peak for eugenyl methyl ether.

The peak indicated by reference numeral 33 is the peak for α-copene.

The peak indicated by reference numeral 34 is the peak for trans-isoeugenol.

The peak indicated by reference numeral 35 is the peak for α-bergamotene.

The peak indicated by reference numeral 36 is the peak for 4-propenyl-1,2-dimethoxy benzene.

The peak indicated by reference numeral 37 is the peak for myristicin.

The peak indicated by reference numeral 38 is the peak for δ-cadinene.

The peak indicated by reference numeral 39 is the peak for elemicine.

The peak indicated by reference numeral 40 is the peak for 4-allyl-2,6-dimethoxyphenol.

Table IV sets forth the head space constituents of nutmeg oil after the 15 minute period using the procedure set forth, supra; after a one hour period, using the procedure set forth, supra, and after a 24 hour period, using the procedure set forth, supra:

TABLE IV

HEADSPACE CONSTITUENTS OF NUTMEG OIL

| Compound | % After 15 Min. | % After 1 Hour | % After 24 Hours |
|---|---|---|---|
| α-Thujene | 2.80 | 2.90 | 2.30 |
| α-Pinene | 25.00 | 25.20 | 20.50 |
| Camphene | 0.40 | 0.40 | 0.32 |
| Sabinene | 25.20 | 24.40 | 21.00 |
| β-Pinene | 20.00 | 18.90 | 16.50 |
| Myrcene | 2.80 | 3.00 | 3.00 |
| α-Phellandrene | 1.00 | 1.00 | 1.10 |
| Δ-3 Carene | 1.00 | 1.00 | 1.00 |
| α-Terpinene | 3.80 | 4.10 | 4.40 |
| P-cymene | 1.30 | 1.40 | 1.41 |
| Limonene | 6.60 | 7.30 | 8.00 |
| γ-Terpinene | 4.50 | 5.10 | 6.80 |
| Terpinolene | 1.20 | 1.40 | 2.20 |
| Linalool | Trace | Trace | 0.50 |
| Terpineol-4 | 1.80 | 2.30 | 6.81 |
| α-Terpineol | Trace | 0.20 | 0.60 |
| Safrole | 0.20 | 0.30 | 1.40 |
| Myristicin | Trace | 0.10 | 0.75 |

For the purpose of the dose calculations, the head space concentrations of myristicin was assumed to be 0.1% of the total nutmeg oil that had evaporated.

Table V summarizes the percent myristicin in the vapor in equilibrium with nutmeg oil or in equilibrium with mace extract after 15 minutes, 1 hour, 2 hours, 3 hours, 4 hours and 24 hours. The analytical procedure for the determination was described previously in this example.

It has been found that neat Nutmeg Oil East Indian contains 7.10% myristicin and mace extract contains 31.00% myristicin.

TABLE V

HEAD SPACE STUDY OF NUTMEG AND MACE

| EVAPORATION TIME | % MYRISTICIN IN THE VAPOR OVER NUTMEG | % MYRISTICIN IN THE VAPOR OVER MACE EXTRACT |
|---|---|---|
| 15 Minutes | Trace | Trace |
| 1 Hour | 0.10 | 0.90 |
| 2 Hours | 0.40 | 2.80 |
| 3 Hours | 0.50 | 5.00 |
| 4 Hours | 0.60 | 7.00 |
| 24 Hours | 0.75 | 8.00 |

Table VI sets forth overall compositions of Nutmeg Oil East Indian, Nutmeg Oil Terpenless and two other commercial nutmeg oils as well as Mace Extract:

TABLE VI

CONSTUTUENTS OF NUTMEG AND MACE OIL

| Compound | NUTMEG OIL EAST INDIAN | NUTMEG OIL TERPENLESS | COMMERICAL NUTMEG OIL SAMPLE X | COMMERICIAL NUTMEG OIL SAMPLE Y | MACE EXTRACT |
|---|---|---|---|---|---|
| α-Thujene | 2.50% | 1.00% | 1.50% | 0.60% | 0.60% |
| α-Pinene | 22.20 | 9.10 | 30.70 | 0.76 | 1.10 |
| Camphene | 0.30 | 0.15 | 0.43 | Trace | — |
| Sabinene | 18.73 | 14.60 | 16.55 | 0.60 | 1.10 |
| β-Pinene | 15.30 | 11.61 | 12.00 | 1.80 | 2.63 |
| Myrcene | 2.50 | 2.70 | 2.00 | 0.50 | 0.74 |
| α-Phellandrene | 0.94 | 1.10 | 0.40 | 0.18 | 0.25 |
| Δ-3-Carene | 0.90 | 0.98 | 0.45 | 1.40 | 0.67 |
| α-Terpinene | 3.70 | 4.60 | 1.64 | 2.30 | 1.30 |
| p-Cymene | 1.00 | 1.74 | 1.72 | — | 1.50 |
| Limonene | 6.60 | 9.40 | 17.63 | 2.90 | 3.00 |
| γ-Terpinene | 5.50 | 8.92 | 2.40 | 2.10 | 2.20 |
| Trans-Sabinene Hydrate | 0.20 | 0.33 | 0.34 | 1.33 | 1.15 |
| α-p-Dimethyl Styrene | 0.07 | 0.12 | Trace | Trace | 0.10 |
| Terpinolene | 1.77 | 3.00 | 0.85 | 0.75 | 1.20 |

TABLE VI-continued
CONSTUTUENTS OF NUTMEG AND MACE OIL

| Compound | NUTMEG OIL EAST INDIAN | NUTMEG OIL TERPENLESS | COMMERICAL NUTMEG OIL SAMPLE X | COMMERICIAL NUTMEG OIL SAMPLE Y | MACE EXTRACT |
|---|---|---|---|---|---|
| Cis-Sabinene Hydrate | 0.15 | 0.30 | 0.20 | 0.80 | 0.80 |
| Linalool | 0.19 | 0.30 | 0.20 | 0.80 | 0.80 |
| Unknown (Two Isomers) | — | — | — | 2.30 | 4.00 |
| 2-p-Menthen-1-ol | 0.14 | 0.25 | 0.16 | Trace | Trace |
| 2-p-Menthen-1-ol (Isomer) | 0.09 | 0.18 | 0.10 | 1.14 | Trace |
| 2-Ethyl-5-Methyl Furan | Trace | Trace | Trace | — | — |
| Terpineol-4 | 6.00 | 10.48 | 3.58 | 6.30 | 3.61 |
| α-Terpineol | 0.70 | 1.28 | 0.47 | 0.70 | 0.60 |
| Piperitol | Trace | Trace | Trace | Trace | Trace |
| Piperitol (Isomer) | Trace | Trace | Trace | Trace | Trace |
| P-Menth-1-en-4-yl-Ethyl Ester | — | — | — | 0.60 | 1.50 |
| Saffole | 1.70 | 3.00 | 1.12 | 3.64 | 4.45 |
| Iso Bornyl Acetate | — | — | — | Trace | Trace |
| Bornyl Acetate | Trace | 0.13 | Trace | Trace | Trace |
| Thymol | — | — | — | Trace | — |
| Amyl Anisol (T) | 0.21 | 0.36 | Trace | Trace | — |
| Eugenol | 0.21 | 0.36 | 0.10 | 0.80 | 1.00 |
| α-Terpinyl Acetate | 0.10 | 0.20 | 0.05 | 0.10 | 0.30 |
| α-Cubebene | 0.05 | 0.10 | Trace | 0.10 | Trace |
| Vanillian | — | — | — | Trace | — |
| Neryl Acetate | 0.10 | 0.17 | 0.08 | 0.10 | Trace |
| Eugenyl Methyl Ether | 0.30 | 0.50 | 0.10 | 1.80 | 1.80 |
| α-Copaene | 0.23 | 0.41 | 0.16 | 0.93 | 0.55 |
| Trans Iso Eugenol | 0.31 | 0.60 | Trace | 0.71 | 3.30 |
| α-Bergamotene | Trace | 0.12 | Trace | Trace | Trace |
| Methyl Iso Eugenol | Trace | Trace | Trace | 0.35 | 0.26 |
| Myristicin | 7.10 | 11.23 | 5.00 | 33.50 | 31.00 |
| Δ-Cadinene | Trace | Trace | Trace | Trace | 0.10 |
| Elemicin | 0.11 | 0.45 | 0.07 | 1.85 | 1.20 |
| Dodecanoic Acid | — | — | — | Trace | — |
| 4-Allyl 2,6-Dimethoxy Phenol | 0.08 | 0.19 | Trace | 2.70 | 5.00 |
| Myristic Acid | — | — | — | 15.32 | — |
| Ethyl Tetradeconate | — | — | — | 5.10 | 2.30 |
| Methyl Octadeconate | — | — | — | 0.85 | 1.00 |
| Ethyl Palmitate | — | — | — | 1.30 | 5.00 |
| Ethyl Oleate | — | — | — | — | 1.50 |
| Octadecenoic Acid Methyl Ester | — | — | — | 1.00 | — |
| | 99.98 | 99.96 | 100.00 | 98.01 | 87.64 |

Trace = <0.01%

EXAMPLE I(C)

Isolation of Elemicin from Oil of Elemi

Elemicin was separated from Oil of Elemi using the following procedure:

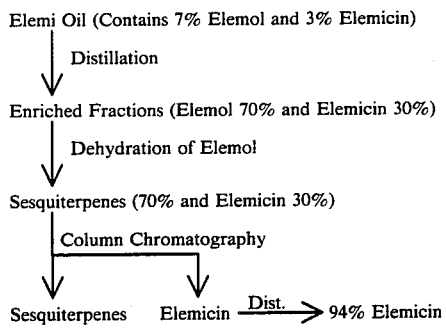

The 94% Elemicin is used in subsequent Examples V, et seq.

EXAMPLE I(D)

Myristicin Synthesis

Myristicin for use in subsequent Examples II, et seq, was synthesized using as a precursor, 1,2-dihydroxy-3-methoxy benzene according to the following reaction sequence:

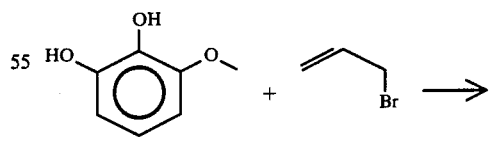

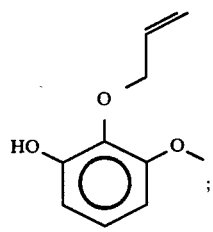

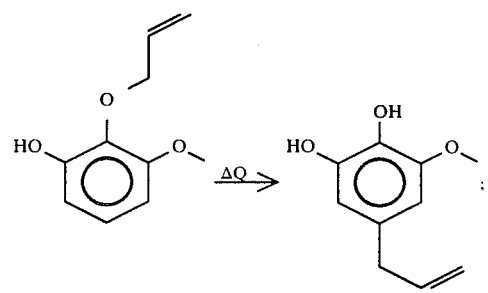

and

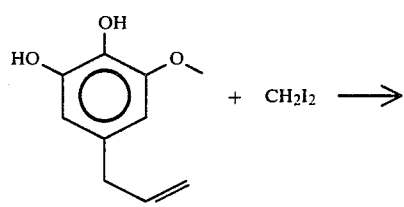

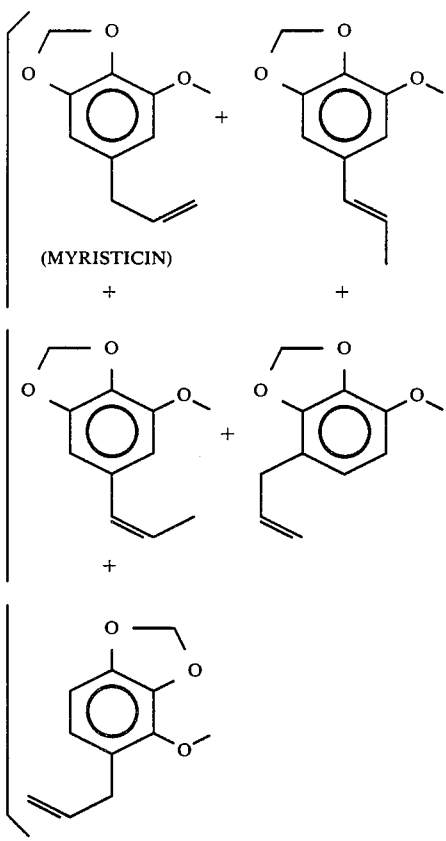

The isolated myristicin was used in Examples V, et seq.

EXAMPLE II

Four odorant conditions were tested using a factorial experimental design. Analysis of the results was by a two way analysis of variance. Factors were Fragrance "A" and "Neutral" Fragrance and levels were +/− the presence of "actives". Analysis of the results was with the BMDP statistical package and a Digital Equipment Co. (DEC) 11/780 VAX computer. An explanation of the analysis of variance (ANOVA) technique is found in:

R. B. McCall, "Fundamental Statistics for Psychology," 2nd Ed., Harcourt Brace Jovanovich, New York, N.Y.; 1975, pages 236–64.

The term "p" is the significance level as obtained from the "F" test applied to the ANOVA results. "p" is the probability that the results obtained are due to random error.

The composition of the fragrances was as follows:

| 1. Fragrance "A" composition: | |
|---|---|
| GALAXOLIDE ® [Registered Trademark of International Flavors & Fragrances Inc.: a tricyclic isochroman having the structure: 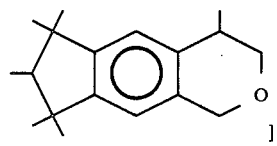 ] | 47.1% |
| Verdox [a chemical manufactured by International Flavors & Fragrances Inc. having the structure: 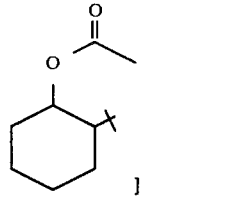 ] | 21.1% |
| Diethyl Phthalate | 12.6% |
| Peach Aldehyde Coeur | 10.5% |
| Prenyl Acetate | 4.0% |
| Hexyl Cinnamic Aldehyde | 2.6% |
| Iso Amyl Butyrate | 1.3% |
| Aldehyde AA-Triplal [a specialty manufactured by International Flavors & Fragrances Inc. having the structure: 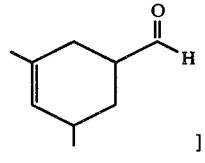 ] | 0.05% |
| Veltol Plus [ethyl maltol having the structure: 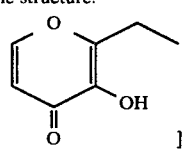 ] | 0.01% |
| 2. "Actives" composition: | |
| Nutmeg Oil East Indian | 97.10% |
| Mace Extract | 0.14% |
| Neroli Oil | 0.98% |
| Diethyl Phthalate | 0.44% |
| Valerian Oil Indian | 0.05% |
| 3. Fragrance + Active: | |
| Fragrance "A" | 60.0% |
| "Actives" | 40.0% |
| 4. "Neutral" Fragrance: | |
| Diethyl Phthalate | 100.0% |
| 5. "Neutral" Fragrance + "Actives": | |
| Diethyl Phthalate | 50.0% |
| Fragrance "A" | 10.0% |
| "Actives" | 40.0% |

The subjects used for the study were drawn from the New Haven, Conn. area. One hundred and twenty subjects were used for the experiment or thirty subjects for each of the four cells. The study was run double blind. Subjects were run at one at a time and the script was presented by tape recorder. Blood pressures and heart rates were measured with an autoinflatable, printing, digital sphygmomanometer manufactured by the Takeda Medical Co., Inc. of Tokyo, Japan.

The protocol allowed for investigation of the cardiovascular and mood responses to a stressor with and without "fragrance" or stress reactivity reducer (SRR) treatments. The objective was to provide a stressor that would produce a stress type and level similar to that experienced in the work place. A further objective was to measure both blood pressure and mood changes during the stress period since the literature has shown that reactivity to stress correlates with disease. The protocol was as follows:
1. Attachment of the blood pressure cuff.
2. Questionnaire.
3. Stress I:
   (a) baseline
   (b) mood self report
   (c) 6 low stress questions (LS1)
   (d) mood self report
   (e) 6 mild stress questions (MS1)
   (f) mood self report
   (g) baseline
   (h) mood self report
4. Treatment:
   (a) Fragrance "A" or
   (b) Fragrance "A"+"Actives" or
   (c) "Neutral" Fragrance or
   (d) "Neutral" Fragrance+"Actives"
5. Stress II:
   (a) baseline
   (b) mood self report
   (c) 6 low stress questions (LS2)
   (d) mood self report
   (e) 6 mild stress questions (MS2)
   (f) mood self report
   (g) base line
   (h) mood self report
6. Post-experimental questionnaire
7. Removal of recording devices and debriefing.

The initial questionnaire contained 53 true/false questions taken from the Marlowe-Crowne repression test and the Bendig form of the Taylor Anxiety Scale. It was used to classify subjects on the basis of repression and anxiety.

Baseline periods involved the subject sitting still, resting. Mood self reports were made by the subject reporting by means of a seven point scale (0-6) his or her degree of relaxation, anger, anxiety, happiness, tenseness, embarrassment, calmness, fear and sleepiness. Neutral and mild stress questions were taken from the Phase Association Test:

Mandler, et al, "Response to Threat: Relations Among Verbal and Physiological Findings" (Psychological Monographs, 1961, Vol. 75, No. 9).

Subjects were asked to respond as quickly as possible with the first phrase that came to mind following presentation of a stimulus phrase. Neutral questions included: "My name is?" Stress phrases included: "The thing I like least about myself is . . . " and "If my child were dating someone of a difference race I would . . . ".

During the treatment period the subject smelled one of the fragrances or postulated stress reactivity reducing agents from a "Measuring Line" style perfume blotter obtained from Frank Orlandi, Inc.: 31-02 Northern Boulevard, Long Island City, Queens, N.Y. 11101. The blotter was about 15 cm long by about 1.4 cm wide. It was dipped into a 20% solution of fragrance and/or postulated stress reactivity reducing agent in ethyl alcohol to a level of about 2 cm (the second red line), allowed to dry for five minutes and then positioned about 6 cm from the subject's nose.

The final questionnaire asked for the subject's reactions to the experiment.

The analysis of variance of the results showed significant changes in systolic blood pressure and self reports for the subjects smelling either fragrance "A" plus "actives" or "neutral" fragrance plus "actives" versus the subjects smelling the fragrance "A" or the "neutral" fragrance alone.

The changes deemed to be relevant to the every day stress and strain of life were the blood pressure and mood changes due to the stress questions relative to the low stress questions ((MS−LS); (see the protocol for definitions of MS and LS). To obtain a Change score for a particular condition the changes before and after the condition were compared thusly:

Change due to the fragrance "A" or "neutral"
fragrance=N; and
N=(MS2−LS2)−(MS1−LS1).

In the same way a change score can be calculated for the fragrance "A" plus "actives" or the "neutral" fragrance plus "actives". This change is referred to as "A".

To obtain the effect of one condition relative to another the change score for one condition can be subtracted from that for another. Thus, the "actives" effect is: (A−N).

For Table VII presented below, the "actives" effect was obtained by pooling the results for the fragrance "A" plus "actives" and "neutral" plus "actives" to obtain "A" and pooling the results for the fragrance "A" and "neutral" fragrances to obtain "N".

In the analysis of variance treatment of the results, the Change score presented below in Table VII is numerically equal to the period by trial by "actives" three-way interactions. In this context, "period" is the average of the effects after treatment relative to the effects before treatment: (LS2+MS2)−(LS1+MS1) averaged across all four treatments. "Trial" is the average of the effects due to mild stress relative to those due to low stress: (MS1+MS2)−(LS1+LS2) averaged across all treatments. "Actives" is the average of effects for the compositions containing "actives" relative to effects for the compositions containing no "actives": (LS1+LS2+MS1+MS2) averaged across fragrance "A"+"actives" and neutral fragrance+"actives" minus (LS1+LS2+MS1+MS2) averaged across fragrance "A" and the neutral fragrance.

TABLE VII

| EFFECT OF "ACTIVES" ON MILD STRESS | | |
|---|---|---|
| VARIABLE | CHANGE ("A"-N) | SIGNIFICANCE LEVEL (p) |
| Systolic Blood Pressure | −4 mm/Hg. | 0.08 |
| Calmness | 0.77 | 0.01 |
| Embarrasment | −2.31 | 0.03 |
| Happiness | 0.77 | 0.0003 |

TABLE VII-continued

| | EFFECT OF "ACTIVES" ON MILD STRESS | |
|---|---|---|
| VARIABLE | CHANGE ("A"-N) | SIGNIFICANCE LEVEL (p) |
| Anger | −0.51 | 0.03 |

Thus, the presence of "actives" in either the fragrance "A" or the "neutral" fragrance decreases systolic blood pressure; increases calmness; decreases embarrassment; increases happiness; and decreases anger.

Even though the subjective results in this case have been quantified, it is important to point out that they also correlated with the systolic blood pressure change.

EXAMPLE III(A)

Two odorant conditions were tested using a factorial experimental design. Analysis of the results by a one way analysis of variance was done. The factor was "fragrance" or "postulated stress reactivity reducing agent"; the levels were plus and minus "actives". The details of the statistical analysis techniques are presented in Example II, supra.

The substances tested were fragrance "A" and a composition of matter composed only of "actives". The composition of the fragrance "A" and of the "actives" are presented in Example II, supra.

The subjects used for the study were drawn from the Union Beach, New Jersey area (Monmouth County in the State of New Jersey). Fourteen subjects were used for the study; seven in each of the two cells. The script was presented by tape recorder and blood pressures were measured with a recording automatic sphygmomanometer as described in Example II, supra. The experimental session periods were the following:

1. Attachment of the blood pressure cuff.
2. Questionnaire.
3. Stress I:
   (a) baseline (BL)
   (b) mood self report
   (c) 6 low stress questions (LS1)
   (d) mood self report
   (e) 6 mild stress questions (MS1)
   (f) mood self report.
4. Treatment:
   (a) fragrance "A" (F) or
   (b) actives fragrance (F).
5. Stress II:
   (a) mood self report
   (b) 6 low stress questions (LS2)
   (c) mood self report
   (d) 6 mild stress questions (MS2)
   (e) mood self report
   (f) baseline (BL2).
6. Post-experimental questionnaire.
7. Removal of recording devices and debriefing.

Details of the parts of the protocol are set forth in Example II, supra. During the treatment period the subjects smelled one of the fragrances or postulated stress reactivity reducing agents from a one dram vial containing a wick saturated with a solution made up of 60% test substance and 40% food grade ethyl alcohol.

The experiment was designed to show the effect of the stressor and (i) fragrance or (ii) stress reactivity reducing agent on systolic blood pressure. The stressor is designed to be mildy frustrating and tension producing. The subject does not have adequate time to answer the questions which are controversial and have complex answers.

FIG. 3 shows the change in systolic blood pressure during the periods of the protocol. For the "before fragrance" or "stress reactivity reducing agent" periods, the moderate stress questions produce about a 5 mm/Hg rise in blood pressure relative to the low stress questions (MS1−LS1). In the after "fragrance" or "stress reactivity reducing agent" periods, the subjects smelling the "actives" experience a 1 mm/Hg decrease in systolic blood pressure during the moderate stress questions relative to the low stress questions while the subjects smelling fragrance "A" experience an 8 mm/Hg increase during the same period (MS2−LS2). The change for the "actives" group relative to the fragrance "A" group as follows:

"Actives" Group:

$$A = (MS2 - LS2) - (MS1 - LS1) = -1 - 5 = -6 \text{ mm/Hg}$$

Non-Actives Group:

$$N = (MS2 - LS2) - (MS1 - LS1) = 8 - 5 = 3 \text{ mm/Hg}$$

Change:

$$A - N = -6 - 3 = -9 \text{ mm/Hg} \; (p = 0.03).$$

The Change score shows that the "Actives" decreases systolic blood pressure during a mildly frustrating event which has been shown in the first part of the experiment to increase systolic blood pressure. The fragrance "A" does not exhibit this effect.

EXAMPLE III(B)

A preferred odorant composition was tested on a Θyear old male subject. The composition of the odorant was 60% fragrance "A" and 40% "actives" (see Example II, supra). The mode of administration was by means of the vial-wick system as described in Example III, supra. The testing protocol was the one described in Example III, supra, and the protocol periods (BL1, LS1, MS1, F, LS2, MS2 and BL2) are also described in Example III. FIG. 4 shows the subject's systolic blood pressure in mm/Hg for each of the periods (indicated by reference numeral 81). The shape of the graph is similar to that for the graph for the "actives" group (indicated by reference numberal 72) presented in FIG. 3. Of particular interest are systolic blood pressure changes between LS1 and MS1 and LS2 and MS2. The subject experienced a 6 mm/Hg increase in systolic blood pressure (MS1−LS1) for the "before fragrance" periods whereas he experienced an 8 mm/Hg decrease (MS2−LS2) for the same periods after the odorant-conditioning period. Hence the Change score (see Example III, supra) is the following:

$$A = (MS2 - MS1) - (MS1 - LS1) = -8 - 6 = -14 \text{ mm/Hg}.$$

This example further shows that the "actives" composition lowers a human's reaction to stress.

EXAMPLE IV(A)

Two odorant conditions were tested using a factorial experimental design. Analysis of the results by a one way analysis of variance was done. The factor was ["fragrance" or postulated stress reactivity reducing "agent"]; the levels were plus and minus "actives". The details of the statistical analysis techniques are presented in Example II, supra.

The substances tested were a composition of matter composed of Ethanol/Distilled Water and a composition of matter composed of Ethanol/"activies". The composition of the "actives" is presented in Example II, supra.

The subjects used for the study were drawn from the Union Beach, New Jersey area (Monmouth County in the State of New Jersey). Thirty subjects were used for the study: fifteen in each of the two cells. The script was presented by tape recorder and blood pressures were measured with a recording automatic sphygmomanometer as described in Example II, supra. The experimental session periods were the following:

1. Attachment of the blood pressure cuff.
2. Questionnaire.
3. Stress I:
    (a) Baseline (BL1)
    (b) mood self report
    (c) 12 mild stress questions (VB1)
    (d) mood self report
    (e) serial counting exercise (MB1)
    (f) mood self report
4. Treatment:
    (a) Ethanol/Water (E) or
    (b) Ethanol/Actives (E+)
5. Stress II:
    (a) Baseline (BL2)
    (b) mood self report
    (c) 12 mild stress questions (VB2)
    (d) mood self report
    (e) serial counting exercise (MB2)
    (f) mood self report
6. Post-experimental questionnaire.
7. Removal of recording devices and debriefing.

The initial questionnaires consist of practice mood evaluations and a number of other questionnaires unrelated to the main experiment.

Baseline periods involved the subject sitting still, resting. The mood self reports were made by the subject reporting by means of a nine point scale (0–9) his or her degree of relaxation, anger, anxiety, happiness, tenseness, embarrassment, calmness, boredom, and excitement. The mild stress questions are as set forth in Example II, supra. The serial counting exercise consisted of asking subjects to write down their responses to a series of instructions such as "count forward from zero by fives". The subjects were informed that they would be given a bonus based on the number of correct operations they performed.

Starting at the beginning of the treatment period, the subjects smelled a fragrance or posulated stress reactivity reducing agents from a one dram vial containing a wool wick saturated with a solution made up of 60% test substance and 40% food grade ethyl alcohol. They continued smelling this fragrance through the end of Stress II.

This protocol was designed to be somewhat more stressful than that set forth in Example II, supra. The "serial counting" is designed to be a measured performance task.

The post-experiment questionnaires consisted of the Marlowe-Crowne/Taylor Anxiety Scale and a questionnaire regarding the subject's reaction to the experiment as set out in Example II, supra.

Two sets of "change scores" are calculated for this experiment in the same manner as set out in Examples II and III, supra. The first is the difference between the baseline and verbal stress values and the second is the difference between the baseline and mathematical stress values as follows:

VB change=(VS2−BS2)−(VS1−BS1)

MB change=(MS2−BS2)−(MS1−BS1)

The effect was then calculated as the difference between the change score for the "active" and that of water. The significance is determined by three-way analysis of variance as set forth in Example II, supra.

TABLE VIII

| | Effect of "Actives" on Stress | | | |
|---|---|---|---|---|
| Variable | VB change | Significance Level (p) | MB change | Significance Level (p) |
| Systolic BP | −6.2 mm/Hg | 0.03 | −1.5 mm/Hg | 0.62 |
| Diastolic BP | −6.7 mm/Hg | 0.05 | −6.4 mm/Hg | 0.09 |
| Relaxed | 1.1 | 0.11 | 1.6 | 0.04 |
| Anxious | −1.1 | 0.12 | −3.1 | 0.002 |
| Tense | −1.6 | 0.08 | −2.3 | 0.06 |
| Embarrassed | −0.7 | 0.45 | −1.5 | 0.04 |
| Bored | 1.9 | 0.06 | 2.4 | 0.06 |

While the level of significance varies between the stressors, the presence of "active" reduces both systolic and diastolic blood pressure; increases relaxation; increases boredom; decreases anxiety; decreases tension and decreases embarrassment.

EXAMPLE IV(B)

Two odorant conditions were tested as set forth in Example IV(A), supra. The treatments tested were fragrance "A" and fragrance ("A"+"actives"). The composition of these is as set forth in Example II, supra.

The subjects used for the study were drawn from the Union Beach, N.J. area (monmouth County in the State of New Jersey). Thirty-five subjects were used for the study: nineteen received fragrance "A" and sixteen fragrance ("A"+"actives").

The change scores and statistical confidences levels were calculated as set forth in Example IV(A). The effect was then calculated as the difference between the change score for ("A"+"actives") and that of "A" alone.

TABLE IX

| | Effect of "A" + "Actives" on Stress | | | |
|---|---|---|---|---|
| Variable | VB change | Significance Level (p) | MB change | Significance Level (p) |
| Systolic BP | −2.6 mm/Hg | 0.39 | −5.2 mm/Hg | 0.18 |
| Diastolic BP | −1.5 mm/Hg | 0.49 | −7.2 mm/Hg | 0.04 |
| Anger | −1.0 | 0.05 | −1.0 | 0.05 |
| Anxiety | −1.2 | 0.04 | −0.3 | 0.70 |
| Happy | 0.8 | 0.27 | 1.1 | 0.13 |
| Tense | −2.0 | 0.04 | −1.5 | 0.13 |

Thus, the presence of "actives" reduces blood pressure; increases happiness; reduces anxiety; reduces tension and reduces anger. This example further shows how the "actives" reduce human stress.

EXAMPLE IV(C)

Two odorant conditions were tested as set forth in Example IV(A), supra. The treatments tested were fragrance "F" and fragrance ("F"+"actives"). The composition of these is as follows:

| 1. Fragrance "F" Composition: | |
|---|---|
| Isobornyl acetate | 19.42% |
| Cedarwood oil | 20.65% |
| Bornyl acetate | 6.75% |
| Pine oil | 6.50% |
| Hexalydro-4,7-methanoindan-5 (or 6)-yl propionate | 3.50% |
| Ethyl acetoacetate | 2.50% |
| α-Terpeneol | 2.38% |
| Methyl nonylacetaldehyde | 1.56% |
| Linalool | 1.62% |
| Coumarin | 1.25% |
| Dipropylene glycol | 33.86% |
| 2. Fragrance "F" + "Actives": | |
| Fragrance "F" | 60.00% |
| Actives (Example II, supra) | 40.00% |

The subjects used for the study were drawn from the Union Beach, N.J. area (Monmouth County in the State of New Jersey). Sixty-five subjects were used for the study: thirty-three received fragrance "F" and thirty-two fragrance ("F"+"Actives").

The change scores and statistical confidences levels were calculated as set forth in Example IV(A). The effect was then calculated as the difference between the change score for ("F"+"Actives") and that of "F" alone.

TABLE IX

Effect of "F" + "Actives" on Stress

| Variable | VB change | Significance Level (p) | MB change | Significance Level (p) |
|---|---|---|---|---|
| Systolic BP | −3.1 mm/Hg | 0.20 | −3.2 mm/Hg | 0.16 |
| Diastolic BP | −4.0 mm/Hg | 0.03 | −4.5 mm/Hg | 0.04 |
| Calm | 1.4 | 0.04 | 1.7 | 0.04 |

Thus, the presence of "actives" reduces blood pressure and increases calmness.

EXAMPLE V

Experiments covered by Examples II, III and IV are carried out using in place of the "Actives" composition the following substantially pure materials:
(i) Nutmeg Oil East Indian;
(ii) Neroli Oil;
(iii) Mace Extract;
(iv) Valerian Oil;
(v) Myristicin;
(vi) Elemicin; and
(vii) Isoelemicin.

Results substantially the same as those obtained in Examples II, III and IV are obtained when using the foregoing pure materials instead of the "actives".

In the following Examples VI, et seq, the following materials are used in perfumed articles causing use of these perfumed articles to create mild stress reactivity reducing effects on the user:

TABLE XI (i) "Actives" composition of Example II;
(ii) Nutmeg Oil East Indian substantially pure;
(iii) Mace Extract substantially pure;
(iv) Neroli Oil;
(v) Valerian Oil;
(vi) Myristicin;
(vii) Elemicin; and
(viii) Isoelemicin.

EXAMPLE VI

Preparation of a Cosmetic Powder Composition

A cosmetic powder is prepared by mixing in a ball mill 100 grams of talcum powder with 0.25 grams of each of the compositions of Table VIII, supra. Each of the cosmetic powders prepared with each of the ingredients of the compositions of matter set forth in Table VIII, supra, creates an effect which can be described as "stress reactivity reducing" in the user.

When each of items (i)–(viii) taken alone is combined at a 50:50 (weight:weight) level with fragrance "A" a pleasant apple aroma is imparted to the cosmetic powder.

EXAMPLE VII

Preparation of a Cologne and Handkerchief Perfume

Each of the compositions of matter of Table VIII, supra, are incorporated into colognes at concentrations of 2.0%, 2.5%, 3.0%, 3.5%, 4.0%, 4.5% and 5.0% in 95% aqueous ethanol together with 4.0%, 4.5% and 5.0% of fragrance "A" of Example II; and into handkerchief perfumes at concentrations of 15%, 20%, 25%, 30% and 40% in 95% aqueous ethanol together with 10% by weight of fragrance "A" of Example II. Distinctive apple aromas are imparted to each of the colognes and handkerchief perfumes and each of the colognes and handkerchief perfumes gives rise to a "stress reactivity-reducing" effect on the user.

EXAMPLE VIII

Deodorant Stick

A deodorant stick composition is prepared containing the following materials:

| INGREDIENTS | PARTS BY WEIGHT |
|---|---|
| Propylene Glycol | 68.00 |
| Sodium Stearate | 7.00 |
| Distilled Water | 23.75 |
| IRGASAN ® DP-300 (2,4,4-trichloro-2'-hydroxy diphenyl ether, manufactured by the Ciba-Geigy Chemical Co. and a Trademark of the Ciba-Geigy Chemical Co.) | 0.25 |
| Composition containing fragrance "A" (50 parts by weight) and one of items (i)–(viii) of Table VIII, supra, (50 parts by weight) | 1.00 |

The ingredients are combined without "active" substance/fragrance composition and heated to 75° C. These ingredients are mixed and continued to be heated until the sodium stearate has dissolved. The resulting mixture is cooled to 40° and the "active" substance/fragrance composition (containing one of the stress reactivity reduction substances of Table VIII, supra) is added and mixed at 40° C. until a suspension is formed.

The resulting suspension is formed into deodorant sticks. On use thereof, users subjected to stress conditions experience reduction in physiological and/or subjective reactivity to stress.

EXAMPLE IX

Solid Room Deodorant Composition

A solid room deodorant composition is preprared as follows:

| INGREDIENTS | PARTS BY WEIGHT |
|---|---|
| PART A: | |
| Distilled Water | 88.45 |
| GELCARIN AFG 15 (Marine Colloids)[1] | 3.00 |
| Formaldehyde | 0.05 |
| PART B: | |
| Glycerine | 3.50 |
| PART C: | |
| Composition containing fragrance "A" (50 parts by weight) and one of items (i)-(viii) of Table VIII, supra (50 parts by weight) | 1.00 |
| PART D: | |
| TWEEN 80 (ICI Americas)[2] | 4.00 |

Notes:
[1]GELCARIN AFG 15 is Carageenan manufactured by Marine Colloids, Inc. Division of FMC Corporation of Springfield, New Jersey 07081.
[2]TWEEN 80 is Polysorbate 80 otherwise known as (polyethylene glycol)$_6$-Sorbitan Oleate, manufactured by ICI Americas Inc. of Wilmington, Delaware 19897.

The composition is prepared by:
1. Heating the water to 85° C. and dispersing the GELCARIN AFG 15 therein;
2. Slowly adding the glycerin while maintaining the mixture at 85° C.;
3. Combining the TWEEN 80 and composition containing "actives" and fragrance;
4. Adding the TWEEN/(fragrance plus "actives") composition to the resulting mixture;
5. Adding formaldehyde to the resulting mixture; and
6. Pouring the resulting mixture into a mold.

The contents are allowed to cool, the mold is opened and the solid "cakes" are removed. The "cakes" are placed into standard air deodorizing apparatus.

On operation of the standard air deodorizing apparatus as a room deodorizer, after four minutes, the room has an aesthetically pleasing apple aroma and further, a person placed in said room who is subject to stress conditions will have a significant stress reactivity reduction.

EXAMPLE X

Body Oil Composition

A body oil composition is prepared as follows:

| INGREDIENTS | PARTS BY WEIGHT |
|---|---|
| Mineral Oil [KLEAROL ® (Witco)] | 45.0 |
| Isopropyl Myristate | 50.0 |
| Composition containing fragrance "A" (50 parts by weight) and one of items (i)-(viii) of Table VIII, supra (50 parts by weight) | 5.0 |

The composition of this example is prepared by combining the ingredients with mixing, ageing and filtering.

Each of the body oil preparations prepared with each of the ingredients of the compositions of matter set forth in Table VIII, supra, creates an effect which can be described as "stress reactivity-reducing" in the user. In addition, a pleasant apple aroma is imparted to the user in each case.

EXAMPLE XI

Hot Oil Treatment Composition (FOR HAIR)

A hot oil treatment composition for hair is prepared as follows:

| PARTS BY WEIGHT | INGREDIENTS |
|---|---|
| 65.9 | UCON Lubricant 50-HB-660[1] (Union Carbide) |
| 30.0 | UCON Lubricant 50-HB-400[2] (Union Carbide) |
| 3.0 | LANTROL AWS (Emery)[3] |
| 0.1 | Propyl Paraben |
| 1.0 | Composition containing fragrance "A" (50 parts by weight) and one of items (i)-(viii) of Table VIII, supra (50 parts by weight) |

Notes:
[1]UCON Lubricant 50-HB-660 is (polypropylene glycol)$_{12}$-butyl ether manufactured by the Union Carbide Corporation of Danbury, Connecticut 06817.
[2]UCON Lubricant 50-HB-400 is (polypropylene glycol)$_9$-butyl ether manufactured by the Union Carbide Corporation of Danbury, Connecticut 06817.
[3]LANTROL AWS is a water dispersable alkoxylated Lanolin oil marketed by Emery Industries of Cincinnati, Ohio 45202.

The composition of this example is prepared by simply adding the ingredients in order while mixing.

Each of the resulting hot oil treatment compositions prepared with each of the ingredients of the cmpositions of matter set forth in Table VIII, supra, creates an effect which can be described as "stress reactivity-reducing" in the user. In addition, a pleasant apple aroma is imparted to the user.

EXAMPLE XII

Aerosol Room Spray Composition

An aerosol room spray composition is prepared as follows:

| INGREDIENTS | PARTS BY WEIGHT |
|---|---|
| SPAN 80[1] | 1.00 |
| Composition containing fragrance "A" (50 parts by weight) and one of items (i)-(viii) of Table VIII, supra (50 parts by weight) | 0.25 |
| Distilled Water | 68.75 |
| Propellant A-46[2] | 30.00 |

Notes:
[1]SPAN 80 is Sorbitan Oleate, manufactured by ICI Americas Inc., of Wilmington, Delaware 19897.
[2]Propellant A-46 is a mixture of 85 weight percent isobutane and 15 weight percent propane.

An aerosol room spray is prepared as follows:
1. adding the water to an aerosol container;
2. mixing the composition containing fragrance "A" and "actives" and the SPAN 80;
3. adding the fragrance/"actives"/SPAN 80 composition to the container;
4. crimping on an aerosol valve;
5. pressurizing the container with Propellant A-46; and
6. fitting an actuator to the valve.

When the resulting composition is sprayed from the aerosol container into a 20'×20'×10' normally ventilated room (T=65° F.), after four minutes, the room has an aesthetically pleasing apple aroma and, further, a person placed in said room who is subjected to stress conditions will have a significant stress reactivity reduction.

What is claimed is:

1. The method of causing the reduction of physiological and/or subjective reactivity to stress in a human being subjected to stress which comprises administering to said human through inhalation a composition of matter consisting of:

(a) from 13 micrograms up to 1000 micrograms of nutmeg oil; and
(b) a carrier perfume composition compatible with said nutmeg oil the weight ratio of said nutmeg oil to said carrier perfume composition being in the range of from 1:100 up to 100:1.

* * * * *